United States Patent
Kondo et al.

(12)

(10) Patent No.: US 6,210,761 B1
(45) Date of Patent: Apr. 3, 2001

(54) LIQUID CRYSTAL COMPOUNDS EXHIBITING NEGATIVE ANISOTROPY OF PERMITTIVITY, LIQUID CRYSTAL COMPOSITIONS, AND LIQUID CRYSTAL DISPLAYS

(75) Inventors: Tomoyuki Kondo; Shuichi Matsui; Kazutoshi Miyazawa; Hiroyuki Takeuchi; Fusayuki Takeshita; Etsuo Nakagawa, all of Chiba (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/319,008

(22) PCT Filed: Nov. 27, 1997

(86) PCT No.: PCT/JP97/04330

§ 371 Date: May 28, 1999

§ 102(e) Date: May 28, 1999

(87) PCT Pub. No.: WO98/23563

PCT Pub. Date: Jun. 4, 1998

(30) Foreign Application Priority Data

Nov. 28, 1996 (JP) .................................................. 8-332767

(51) Int. Cl.[7] .......................... C09K 19/12; C09K 19/52; C07C 25/13
(52) U.S. Cl. ................ 428/1.1; 252/299.01; 252/299.61; 252/299.63; 252/299.66; 570/127; 570/129
(58) Field of Search ........................ 252/299.66, 299.01, 252/299.61, 299.63; 428/1.1; 570/127, 129

(56) References Cited

U.S. PATENT DOCUMENTS 5,279,764 * 1/1994 Reiffenrath et al. ............ 252/299.66
5,820,786 * 10/1998 Sage et al. ...................... 252/299.66

FOREIGN PATENT DOCUMENTS

| 3839213 | 5/1990 | (DE) . |
|---|---|---|
| 1-157925 | 6/1989 | (JP) . |
| 2-501311 | 5/1990 | (JP) . |
| 3-500413 | 1/1991 | (JP) . |
| 4-54146 | 2/1992 | (JP) . |
| 4-103554 | 4/1992 | (JP) . |
| 4-169573 | 6/1992 | (JP) . |
| 4-198140 | 7/1992 | (JP) . |
| 4-282355 | 10/1992 | (JP) . |
| 9-137164 | 5/1997 | (JP) . |
| 9-157202 | 6/1997 | (JP) . |

* cited by examiner

*Primary Examiner*—Shean C. Wu
(74) *Attorney, Agent, or Firm*—Wenderoth, Lind & Ponack, L.L.P.

(57) ABSTRACT

The present invention is to provide liquid crystalline compounds which exhibit a negative dielectric anisotropy value, have an extremely high voltage holding ratio and a low threshold voltage, are remarkably small in their dependency on temperature, hardly exhibit smectic phase, and are excellent in miscibility with other liquid crystal materials; to provide liquid crystal compositions comprising the liquid crystalline compound; and to provide liquid crystal display devices fabricated by using the liquid crystal composition; the liquid crystalline compounds are expressed by the following general formula (1)

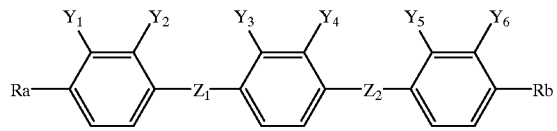

(1)

wherein Ra, Rb, $Y_1$ to $Y_6$, $Z_1$ and $Z_2$ are herein defined.

12 Claims, No Drawings

LIQUID CRYSTAL COMPOUNDS EXHIBITING NEGATIVE ANISOTROPY OF PERMITTIVITY, LIQUID CRYSTAL COMPOSITIONS, AND LIQUID CRYSTAL DISPLAYS

This application is a 371 application of International Application No. PCT/JP97/04330 filed Nov. 27, 1997.

TECHNICAL FIELD

The present invention relates to novel liquid crystalline compounds and liquid crystal compositions. More specifically, it relates to liquid crystalline compounds having a fluorine substituted-1,4-phenylene group, liquid crystal compositions comprising the compound, and liquid crystal display devices fabricated by using the liquid crystal composition.

BACKGROUND ART

Display devices comprising liquid crystalline compounds (the term "liquid crystalline compounds" is used in this specification as a general term for the compounds which exhibit a liquid crystal phase and for the compounds which do not exhibit a liquid crystal phase but are useful as a component of liquid crystal compositions) have widely been utilized for the display of watches, tabletop calculators, word processors, or the likes. In connection with the display devices, researches on in-plane switching (IPS) mode and vertical alignment (VA) mode by which characteristics of viewing angle can be improved at a low manufacturing cost are extensively conducted in recent years.

In liquid crystal compositions for the IPS mode or VA mode, those having a negative dielectric anisotropy value are preferable, and such physical properties as a high voltage holding ratio, low threshold voltage, their small temperature dependency, wide temperature range of liquid crystal phase, excellent miscibility with other liquid crystal materials, and low viscosity are sought for the compositions.

As a component of such liquid crystal compositions, many liquid crystalline compounds in which fluorine atom substituted at their lateral position were investigated and, for example, the following compounds are disclosed in the literatures.

1) (Japanese Patent Application Laid-open No. Hei 2-4725)

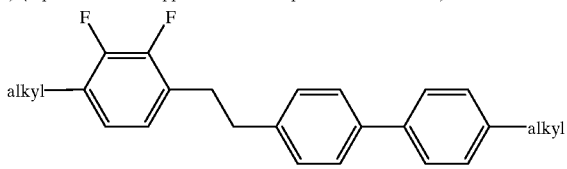

2) (Japanese Patent Application Laid-open No. Hei 4-54146)

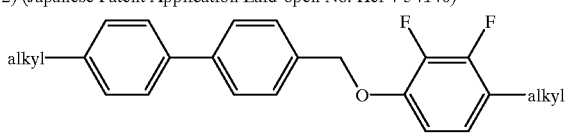

3) (DE 3,839,213 A1)

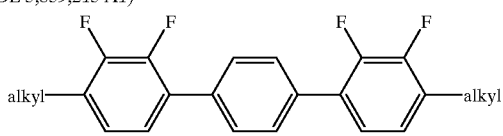

However, they have such problems that the compounds of 1) are high in threshold voltage and that the compounds of 2) and 3) are low in transition temperature to isotropic phase or tend to exhibit smectic phase, and thus the compounds of 2) and 3) hardly from a stable nematic phase particularly at low temperatures when used as component of liquid crystal compositions.

DISCLOSURE OF THE INVENTION

In view of such characteristics required of liquid crystal compositions as described above, an object of the present invention is to provide liquid crystalline compounds which exhibit a negative dielectric anisotropy value, have an extremely high voltage holding ratio and a low threshold voltage, are remarkably small in their dependency on temperature, hardly exhibit smectic phase, and are excellent in miscibility with other liquid crystal materials; to provide liquid crystal compositions comprising the liquid crystalline compound; and to provide liquid crystal display devices fabricated by using the liquid crystal composition.

As a result of diligent investigation by the present inventors to solve the subjects described above, it has been found that

[1] the liquid crystalline compounds expressed by the general formula (1)

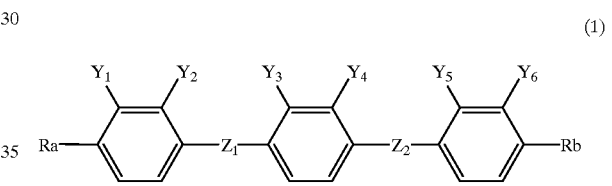

(1)

wherein Ra and Rb independently represent a straight chain or branched alkyl group having 1 to 20 carbon atoms in which alkyl group any non-adjacent methylene group (—CH$_2$—) may be replaced by oxygen atom; $Y_1$, $Y_2$, $Y_3$, $Y_4$, $Y_5$, and $Y_6$ each independently represent hydrogen atom or fluorine atom provided that at least three of $Y_1$, $Y_2$, $Y_3$, $Y_4$, $Y_5$, and $Y_6$ represent fluorine atom; $Z_1$ and $Z_2$ each independently represent —(CH$_2$)$_2$—, —(CH$_2$)$_4$—, —CH$_2$O—, —(CH$_2$)$_3$O—, or single bond provided that in no case represent $Z_1$ and $Z_2$ simultaneously single bond; and any atom which constitutes the compound may be replaced by its isotope, have expected properties, leading to the accomplishment of the present invention.

Also, the present invention has the following aspects:

[2] The liquid crystalline compound recited in aspect [1] above wherein at least one of $Z_1$ and $Z_2$ is —(CH$_2$)$_2$— or —CH$_2$O—.

[3] A liquid crystal composition comprising at least one liquid crystalline compound recited in claim aspect [1] or [2] above.

[4] A liquid crystal composition comprising, as a first component, at least one liquid crystalline compound recited in aspect [1] or [2] above, and comprising, as a second component, at least one compound selected from the group consisting of the compounds expressed by any one of the general formulas (2), (3) and (4)

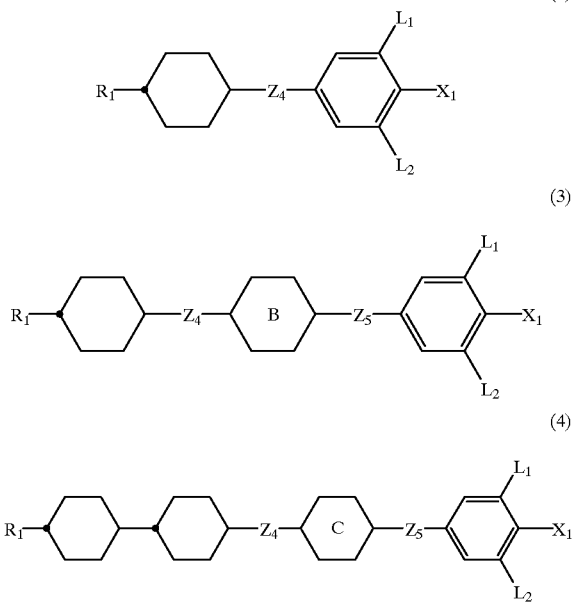

(2)

(3)

(4)

wherein $R_1$ represents an alkyl group having 1 to 10 carbon atoms in which alkyl group any non-adjacent methylene group may be replaced by oxygen atom or —CH=CH—, and any hydrogen atom in which alkyl group may be replaced by fluorine atom; $X_1$ represents fluorine atom, chlorine atom, —OCF$_3$, —OCF$_2$H, —CF$_3$, —CF$_2$H, —CFH$_2$, —OCF$_2$CF$_2$H or —OCF$_2$CFHCF$_3$; $L_1$ and $L_2$ each independently represent hydrogen atom or fluorine atom; $Z_4$ and $Z_5$ each independently represent —(CH$_2$)$_2$—, —(CH$_2$)$_4$—, —COO—, —CF$_2$O—, —OCF$_2$—, —CH=CH— or single bond; ring B represents 1,4-phenylene in which hydrogen atom may be replaced by fluorine atom, trans-1,4-cyclohexylene or 1,3-dioxane-2,5-diyl; ring C represents trans-1,4-cyclohexylene or 1,4-phenylene in which phenylene hydrogen atom may be replaced by fluorine atom; and any atom which constitutes these compounds may be replaced by its isotope.

[5] A liquid crystal composition comprising, as a first component, at least one liquid crystalline compound recited in aspect [1] or [2] above, and comprising, as a second component, at least one compound selected from the group consisting of the compounds expressed by the general formula (5) or (6)

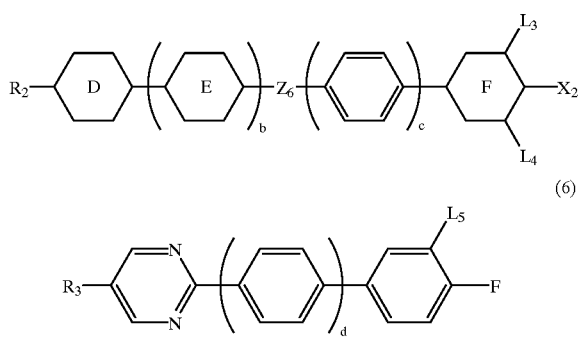

(5)

(6)

wherein $R_2$ and $R_3$ each independently represent an alkyl group having 1 to 10 carbon atoms in which alkyl group any non-adjacent methylene group may be replaced by oxygen atom or —CH=CH, and any hydrogen atom in which alkyl group may be replaced by fluorine atom; $X_2$ represents —CN group or —C≡C—CN; ring D represents trans-1,4-cyclohexylene, 1,4-phenylene, 1,3-dioxane-2,5-diyl or pyrimidine-2,5-diyl; ring E represents 1,4-phenylene in which hydrogen atom may be replaced by fluorine atom, trans-1,4-cyclohexylene or pyrimidine-2,5-diyl; ring F represents trans-1,4-cyclohexylene or 1,4-phenylene; $Z_6$ represents —(CH$_2$)$_2$—, —COO— or single bond; $L_3$, $L_4$ and $L_5$ each independently represent hydrogen atom or fluorine atom; b, c and d are each independently 0 or 1; and any atom which constitutes these compounds may be replaced by its isotope.

[6] A liquid crystal composition comprising, as a first component, at least one liquid crystalline compound recited in aspect [1] or [2] above, comprising, as a second component, at least one compound selected from the group consisting of the compounds expressed by any one of the general formulas (2), (3) and (4) described above, and comprising, as a third component, at least one compound selected from the group consisting of the compounds expressed by any one of the general formula (7), (8) and (9)

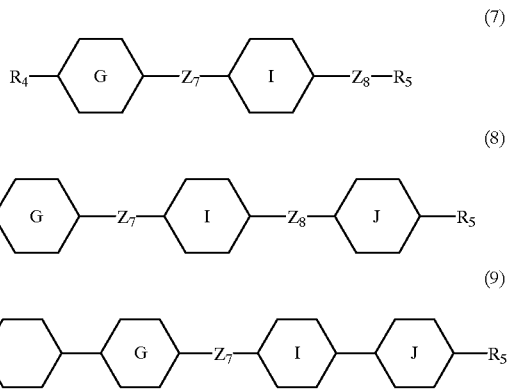

(7)

(8)

(9)

wherein $R_4$ and $R_5$ each independently represent an alkyl group having 1 to 10 carbon atoms in which alkyl group any non-adjacent methylene group may be replaced by oxygen atom or —CH=CH—, and any hydrogen atom in which alkyl group may be replaced by fluorine atom; ring G, ring I and ring J each independently represent 1,4-phenylene in which hydrogen atom may be replaced by fluorine atom, trans-1,4-cyclohexylene or pyrimidine-2,5-diyl; $Z_7$ and $Z_8$ independently represent —C≡C—, —COO—, —(CH$_2$)$_2$—, —CH=CH— or single bond; and any atom which constitutes these compounds may be replaced by its isotope.

[7] A liquid crystal composition comprising, as a first component, at least one liquid crystalline compound recited in aspect [1] or [2] above, comprising, as a second component, at least one compound selected from the group consisting of the compounds expressed by the general formula (5) or (6) described above, and comprising, as a third component, at least one compound selected from the group consisting of the compounds expressed by any one of the general formulas (7), (8) and (9) described above.

[8] A liquid crystal composition comprising, as a first component, at least one liquid crystalline compound recited in aspect [1] or [2] above, and comprising, as a second component, at least one compound selected from the group consisting of the compounds expressed by any one of the general formulas (10), (11) and (12)

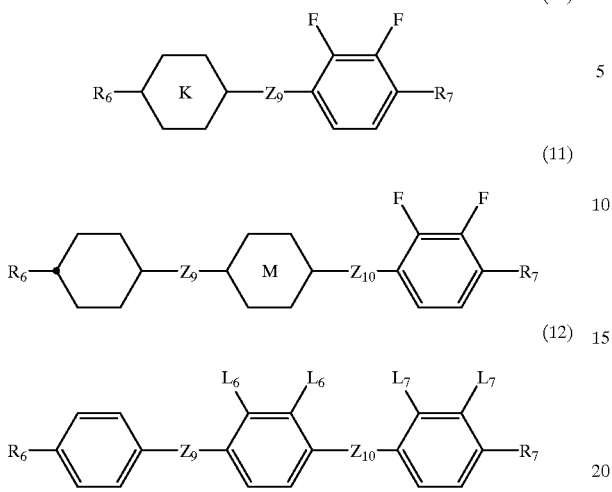

wherein $R_6$ and $R_7$ each independently represent an alkyl group having 1 to 10 carbon atoms in which alkyl group any non-adjacent methylene group may be replaced by oxygen atom or —CH=CH—, and any hydrogen atom in the alkyl group may be replaced by fluorine atom; ring K and ring M each independently represent trans-1,4-cyclohexylene or 1,4-phenylene; $L_6$ and $L_7$ each independently represent hydrogen atom or fluorine atom provided that in no case represent $L_6$ and $L_7$ simultaneously hydrogen atom; $Z_9$ and $Z_{10}$ each independently represent —$(CH_2)_2$—, —COO— or single bond; and any atom which constitutes these compounds may be replaced by its isotope.

[9] A liquid crystal composition comprising, as a first component, at least one liquid crystalline compound recited in aspect [1] or [2] above, comprising, as a second component, at least one compound selected from the group consisting of the compounds expressed by any one of the general formulas (7), (8) and (9) described above, and comprising, as a third component, at least one compound selected from the group consisting of the compounds expressed by any one of the general formulas (10), (11) and (12) described above.

[10] A liquid crystal composition comprising, as a first component, at least one liquid crystalline compound recited in aspect [1] or [2] above, comprising, as a second component, at least one compound selected from the group consisting of the compounds expressed by any one of the general formulas (2), (3) and (4) described above, comprising, as a third component, at least one compound selected from the group consisting of the compounds expressed by the general formula (5) or (6) described above, and comprising, as a fourth component, at least one compound selected from the group consisting of the compounds expressed by any one of the general formulas (7), (8) and (9) described above.

[11] A liquid crystal composition further comprising one or more optically active compounds in addition to the liquid crystal composition defined in any one of aspects [3] to [10] above.

[12] A liquid crystal display device fabricated by using the liquid crystal composition defined in any one of aspects [3] to [11] above.

Whereas a part of the compounds expressed by the general formula (1) are formally included in the claims or disclosure of the literature 1) or 3) described above; such data as physical property values are not described at all in the literatures in relation to the compounds of the present invention, specific references to the characteristics of the compounds are not included therein, and thus the literatures do not suggest the utility of the compounds of the present invention.

Compounds expressed by the general formula (1) are classified into the following (a-1) to (a-24):

Ra—B—$(CH_2)_2$—B—B—Rb (a-1)
Ra—B—$(CH_2)_4$—B—B—Rb (a-2)
Ra—B—$CH_2O$—B—B—Rb (a-3)
Ra—B—$OCH_2$—B—B—Rb (a-4)
Ra—B—$(CH_2)_3O$—B—B—Rb (a-3)
Ra—B—$O(CH_2)_3$—B—B—Rb (a-6)
Ra—B—$(CH_2)_2$—B—$(CH_2)_2$—B—Rb (a-7)
Ra—B—$(CH_2)_2$—B—$(CH_2)_4$—B—Rb (a-8)
Ra—B—$(CH_2)_4$—B—$(CH_2)_4$—B—Rb (a-9)
Ra—B—$(CH_2)_2$—B—$CH_2O$—B—Rb (a-10)
Ra—B—$(CH_2)_2$—B—$OCH_2$—B—Rb (a-11)
Ra—B—$(CH_2)_2$—B—$(CH_2)_3O$—B—Rb (a-12)
Ra—B—$(CH_2)_2$—B—$O(CH_2)_3$—B—Rb (a-13)
Ra—B—$(CH_2)_4$—B—$CH_2O$—B—Rb (a-14)
Ra—B—$(CH_2)_4$—B—$OCH_2$—B—Rb (a-15)
Ra—B—$(CH_2)_4$—B—$(CH_2)_3O$—B—Rb (a-16)
Ra—B—$(CH_2)_4$—B—$O(CH_2)_3$—B—Rb (a-17)
Ra—B—$CH_2O$—B—$CH_2O$—B—Rb (a-18)
Ra—B—$CH_2O$—B—$OCH_2$—B—Rb (a-19)
Ra—B—$OCH_2$—B—$CH_2O$—B—Rb (a-20)
Ra—B—$CH_2O$—B—$(CH_2)_3O$—B—Rb (a-21)
Ra—B—$CH_2O$—B—$O(CH_2)_3$—B—Rb (a-22)
Ra—B—$OCH_2$—B—$(CH_2)_3O$—B—Rb (a-23)
Ra—B—$OCH_2$—B—$O(CH_2)_3$—B—Rb (a-24)

wherein Ra and Rb have the same meaning as described above, and B represents 1,4-phenylene in which at least one hydrogen atom on the ring may be replaced by fluorine atom.

Any compounds expressed by one of the formulas (a-1) to (a-24) exhibit preferable properties. Among them, however, compounds expressed by one of the formulas (a-1) to (a-4), (a-10), and (a-11) can be mentioned as ones exhibiting more preferable properties.

In the formulas, Ra and Rb represent a straight chain or branched alkyl group having 1 to 20 carbon atoms. As the straight chain alkyl group, methyl, ethyl, propyl, butyl, pentyl, hexyl, heptyl, decyl, pentadecyl, icosyl and the like can specifically be mentioned as examples. As the branched alkyl group, isopropyl, sec-butyl, tert-butyl, 2-methylbutyl, isopentyl, isohexyl, 3-ethyloctyl, 3,8-dimethyltetradecyl, 5-ethyl-5-methylnonadecyl and the like can specifically be mentioned as examples. Compounds having the branched alkyl group may exhibit optical activity, and such compounds are useful as chiral dopant.

Any non-adjacent methylene group in these alkyl groups may be replaced by oxygen atom. Specifically, alkoxy groups such as methoxy, ethoxy, propoxy, butoxy, pentyloxy, and nonyloxy and alkoxyalkyl groups such as methoxymethyl, methoxyethyl, methoxypropyl, methoxybutyl, methoxypentyl, methoxyoctyl, ethoxymethyl, ethoxyethyl, ethoxypropyl, ethoxyhexyl, propoxymethyl, propoxyethyl, propoxypropyl, propoxypentyl, butoxymethyl, butoxyethyl, butoxybutyl, pentyloxymethyl, pentyloxybutyl, hexyloxymethyl, hexyloxyethyl, hexyloxypropyl, heptyloxymethyl and octyloxymethyl can be mentioned as their examples.

While the liquid crystalline compounds of the present invention expressed by the general formula (1) can be produced by methods of ordinary organic synthesis, they can conveniently be produced, for instance, by the following method:

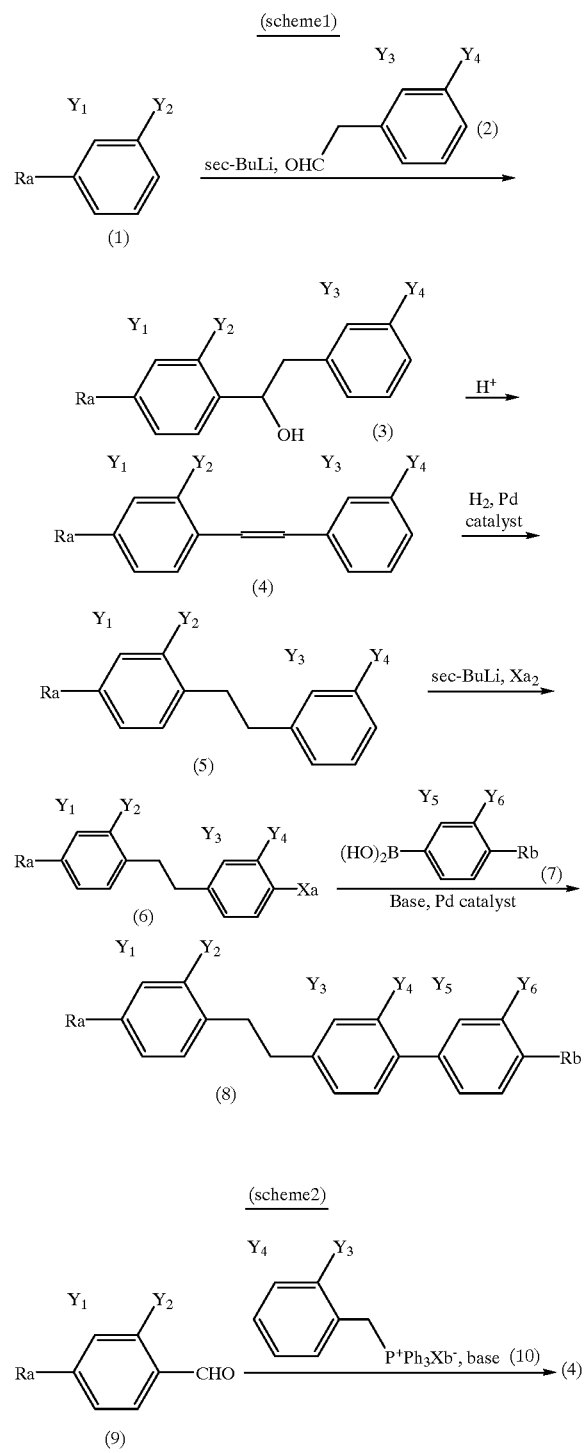

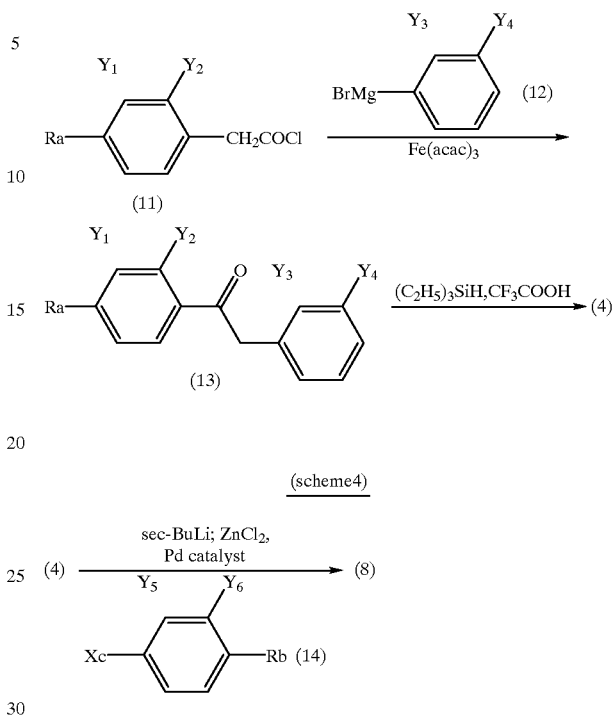

wherein Ra, Rb and $Y_1$ to $Y_6$ have the same meaning as described above, and Xa to Xc represent a halogen atom.

That is, as shown in scheme 1, compound (1), a lithium compound such as n-butyl lithium and sec-butyl lithium (sec-BuLi) (alternatively, a corresponding Grignard reagent may be used), and compound (2) are reacted to obtain compound (3). Compound (3) is dehydrated in a solvent such as toluene and xylene in the presence of an acid catalyst such as p-toluenesulfonic acid, and then subjected to hydrogenation in the presence of a palladium catalyst, Raney-nickel catalyst and the like to obtain compound (5). Compound (5), a lithium compound such as n-butyl lithium and sec-butyl lithium, and a halogen molecule (particularly, bromine or iodine) are reacted to obtain compound (6). Subsequently, compound (6) can be reacted with dihydroxyborane derivative (7) in a mixed solvent of toluene, xylene, or the like, an alcohol such as ethanol, and water in the presence of a base such as $K_2CO_3$ and $Na_2CO_3$, and a catalyst such as a palladium carried on carbon (Pd—C), $Pd(PPh_3)_4$ and $PdCl_2(PPh_3)_2$ (M. Hird et al., Liquid Crystals, 18 (1), 1 (1995)) to produce compound (8) of the present invention.

As shown in scheme 2, compound (8) of the present invention can be produced by preparing compound (4) by the Wittig reaction (Organic Reactions, Vol. 14, Chapter 3) between compound (9) and compound (10), and then treating compound (4) in the same way as in scheme 1.

As shown in scheme 3, compound (8) of the present invention can be produced by reacting compound (11) with compound (12) (C. Cardellicchio et al., Tetrahedron Letters, 28 (18), 2053 (1987)) to form compound (13), subjecting it to a reducing reaction with a hydrosilane or the like (C. T. West et al., The Journal of Organic Chemistry, 38, 2675 (1973)) to obtain compound (4), and then treating compound (4) in the same way as in scheme 1.

Alternatively, as shown in scheme 4, compound (8) of the present invention can also be produced by reacting compound (4), a lithium compound such as n-butyl lithium and sec-butyl lithium, and a zinc compound such as $ZnCl_2$ and $ZnBr_2$, and then subjecting to coupling reaction with compound (14) (Hayashi et al., The Journal of the American Chemical Society, 106, 158 (1984)).

Whereas the reactions described above are all known in public, it is needless to say that other known reactions can further be used when necessary.

The liquid crystalline compounds of the present invention obtained by such methods have an extremely high voltage holding ratio and a low threshold voltage, are remarkably low in their dependency on temperature, hardly exhibit

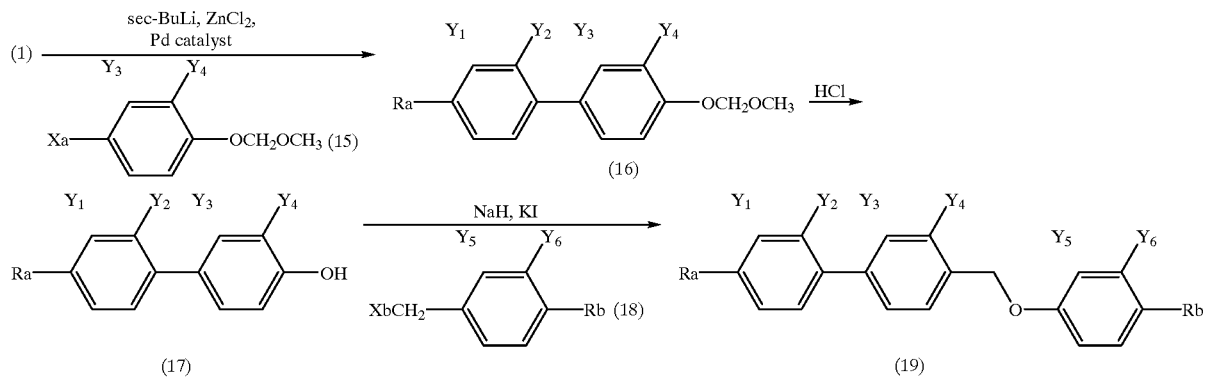

Further, as shown in scheme 5, first, compound (17) is obtained by obtaining compound (16) by a coupling reaction between compound (1) and phenol derivative (15) protected with a protecting group such as methyl group and methoxymethyl group, and then deprotecting compound (16). Subsequently, compound (17) can be reacted with compound (18) in a solvent such as dimethyl sulfoxide, dimethyl formamide, 1,2-dimethoxyethane, tetrahydrofuran, hexamethylphosphoric triamide, and toluene in the presence of a base such as sodium amide (J. B. Wright et al., Journal of the American Chemical Society, 70, 3098 (1948)), sodium carbonate (W. T. Olson et al., Journal of the American Chemical Society, 69, 2451 (1947)), triethylamine (R. L. Merker et al., The Journal of Organic Chemistry, 26, 5180 (1961)), sodium hydroxide (C. Wilkins, Synthesis, 156, (1973)), potassium hydroxide (J. Rebek et al., The Journal of Organic Chemistry, 44, 1485 (1979)), barium hydroxide (Kawabe et al., The Journal of Organic Chemistry, 37, 4210 (1972)), and sodium hydride (NaH) (C. J. Stark, Tetrahedron Letters, 22, 2089 (1981), and K. Takai et al., Tetrahedron Letters, 21, 1657 (1980)) to produce compound (19) of the present invention.

Compounds expressed by the general formula (1) wherein Ra has —O— therein can be produced by similar methods.

While dihydroxyborane derivative (7) which is a starting material can be produced by known general methods of organic synthesis, it can conveniently be produced, for example, by the following method:

(scheme 6)

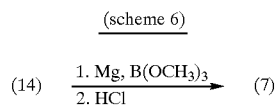

That is, as shown in scheme 6, dihydroxyborane derivative (7) can be produced by reacting halogen compound (14), a Grignard reagent prepared from magnesium, and a trialkoxyborane such as trimethoxyborane and triisopropyloxy-borane and then hydrolyzing the reaction product with hydrochloric acid, sulfuric acid, or the like.

smectic phase, and are excellent in miscibility with other liquid crystal materials. Besides, these liquid crystalline compounds of the present invention are sufficiently stable chemically and physically under conditions wherein liquid crystal display devices are ordinarily used, and are considerably excellent as component of nematic liquid crystal compositions.

The compounds of the present invention can suitably be used as component even in liquid crystal compositions for TN, STN or TFT.

Compounds expressed by the general formula (1) exhibit a comparatively high transition temperature to isotropic phase and a low viscosity.

Further, the compounds having the following partial structure exhibit a particularly high and negative dielectric anisotropy value.

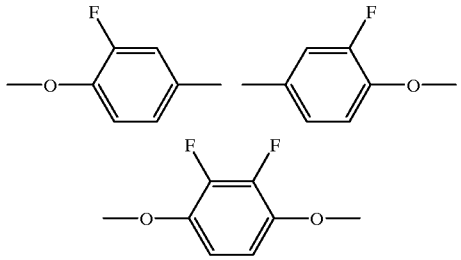

By replacing the hydrogen atom in the ring structure to fluorine atom, it becomes possible to let the compounds have a larger dielectric anisotropy value, and their miscibility can simultaneously be improved.

Moreover, the compounds of the present invention wherein an atom therein is replaced by its isotope can be said to be preferable since such compounds exhibit similar properties.

Based on the facts described above, new liquid crystalline compounds having desired physical properties can be obtained by selecting a proper ring, lateral chain, substituent, and bonding group.

Now, the liquid crystal compositions of the present invention are described. In order to let the compositions develop excellent properties, it is preferable that the liquid crystal compositions of the present invention comprise at least one compound expressed by the general formula (1) in a ratio of 0.1 to 99.9% by weight, and the ratio is more preferably 1 to 60% by weight.

More specifically, the liquid crystal compositions provided according to the present invention are completed by mixing a compound which is selected, depending on the purposes of the liquid crystal compositions, from the group of compounds expressed by one of the general formulas (2) to (12), to a first component comprising at least one compound expressed by the general formula (1).

As preferable examples of the compounds used for the liquid crystal compositions of the present invention and expressed by one of the general formulas (2) to (4), the following compounds can be mentioned:

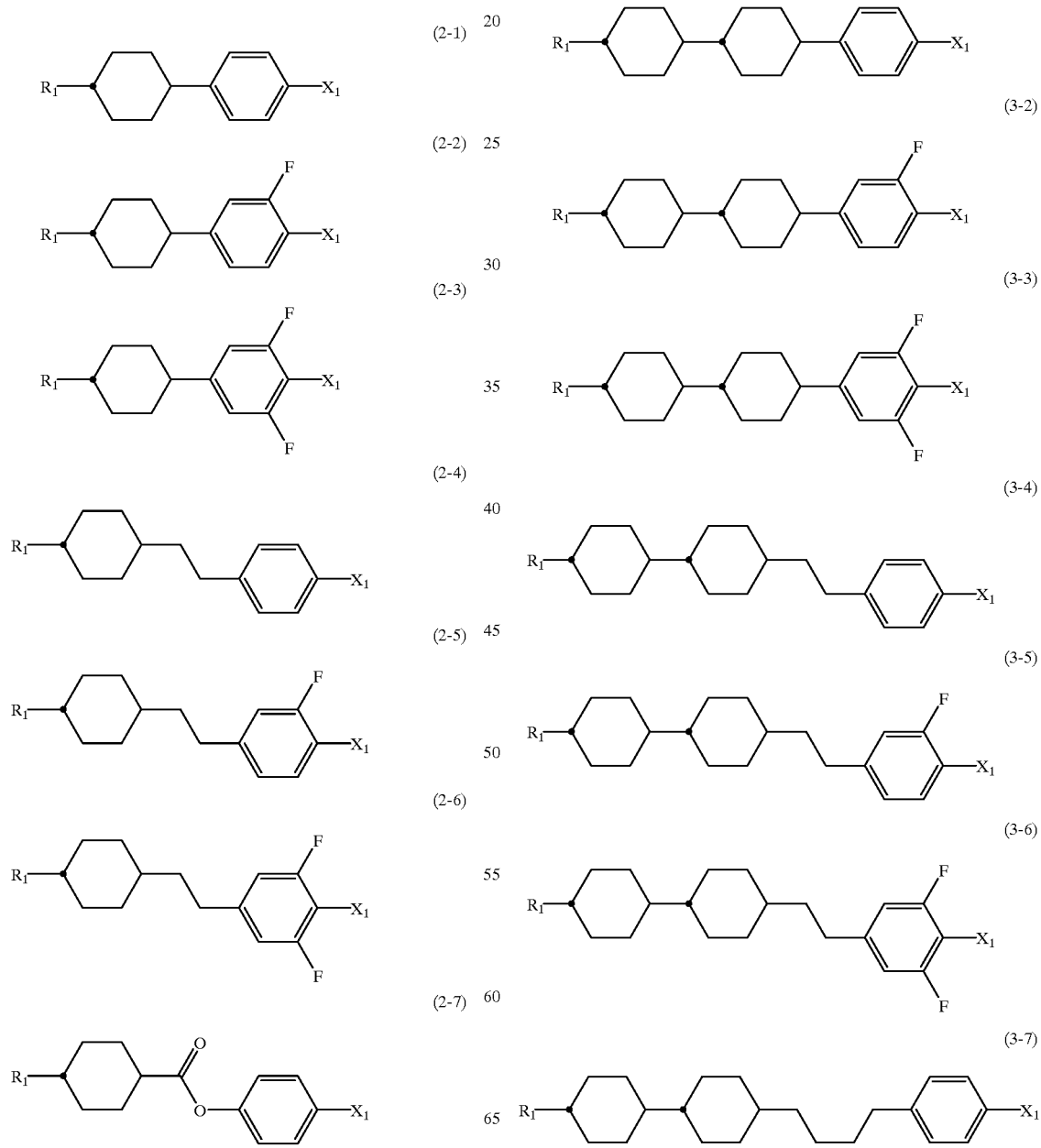

(3-8) 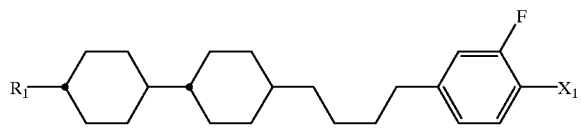
(3-9) 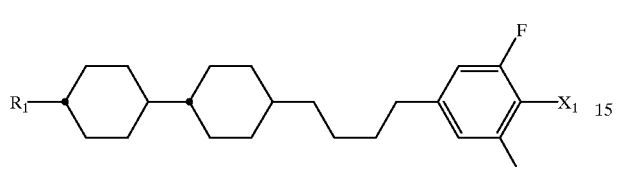
(3-10) 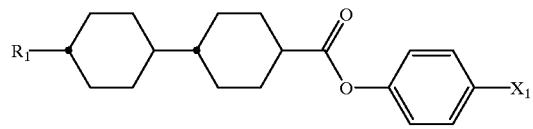
(3-11) 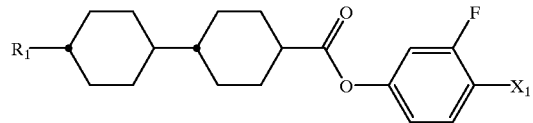
(3-12) 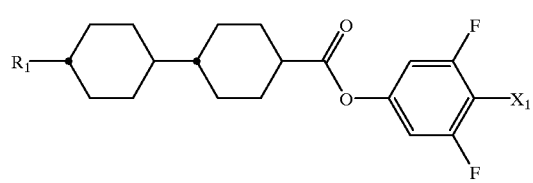
(3-13) 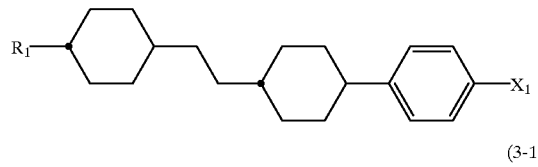
(3-14) 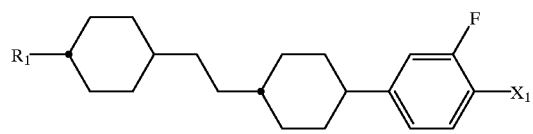
(3-15) 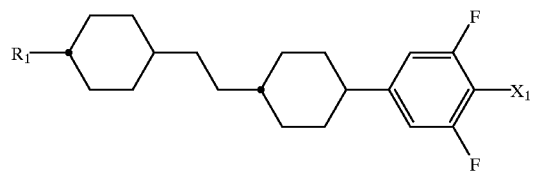
(3-16) 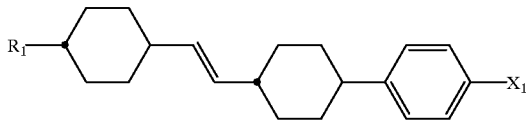
(3-17) 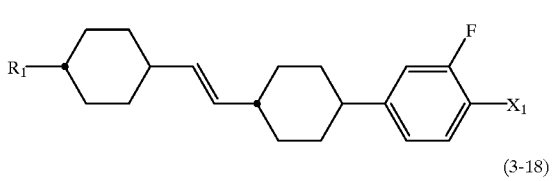
(3-18) 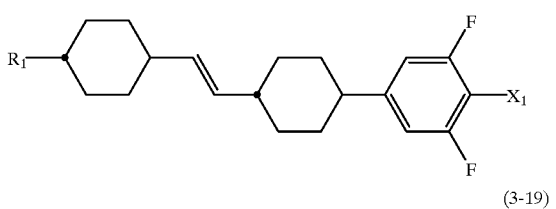
(3-19) 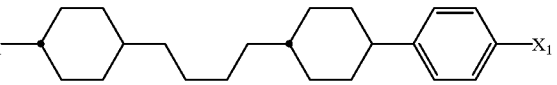
(3-20) 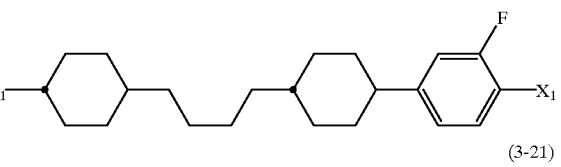
(3-21) 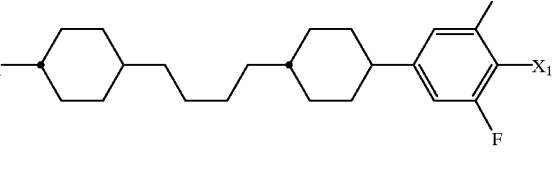
(3-22) 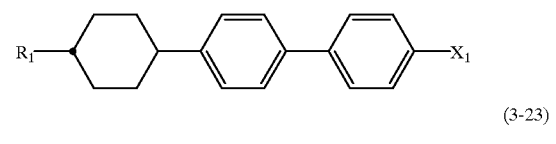
(3-23) 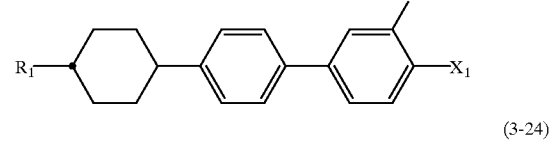
(3-24) 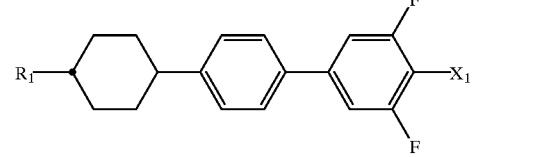

(3-25)
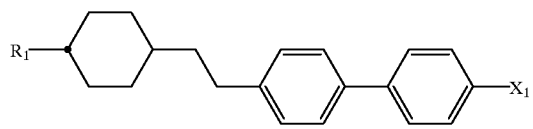
(3-26)
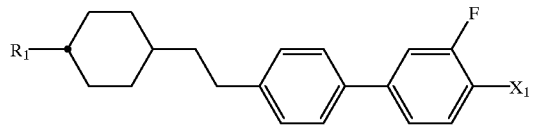
(3-27)
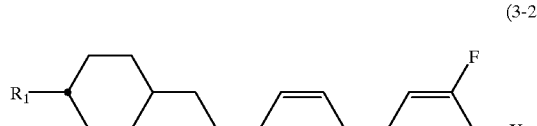
(3-28)
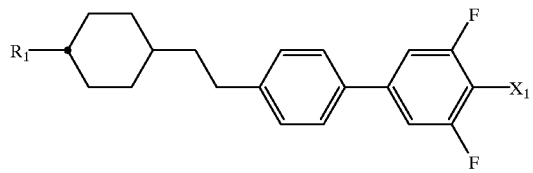
(3-29)
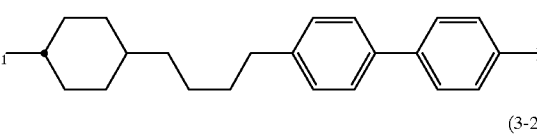
(3-30)
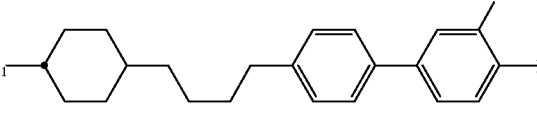
(3-31)
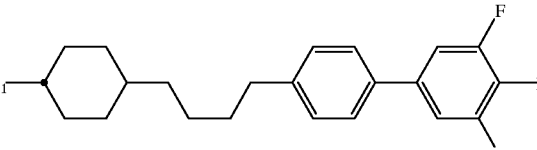
(3-32)
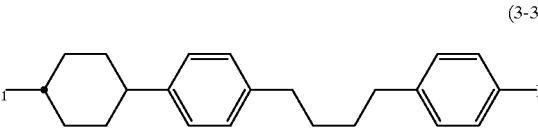
(3-33)
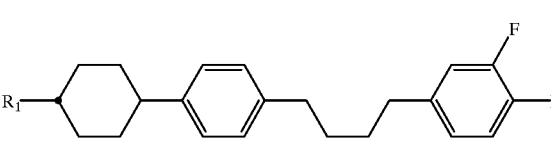
(3-34)
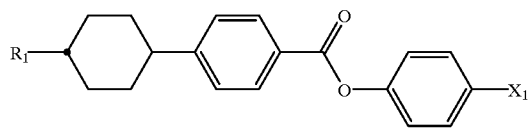
(3-35)
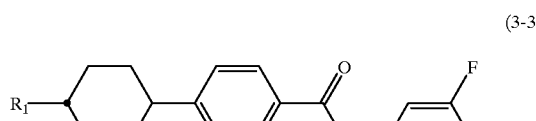
(3-36)
(3-37)
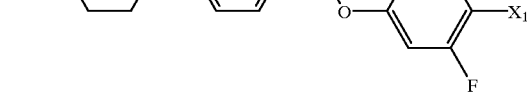
(3-38)
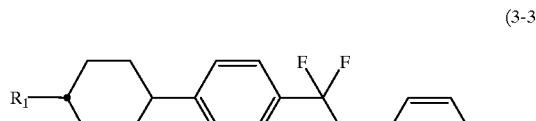
(3-39)
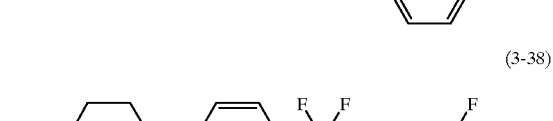
(3-40)
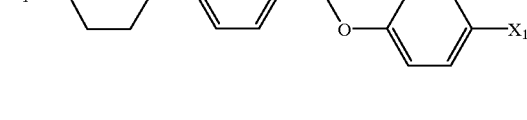
(3-41)
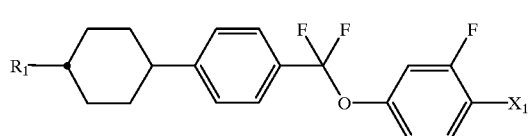

(3-42)
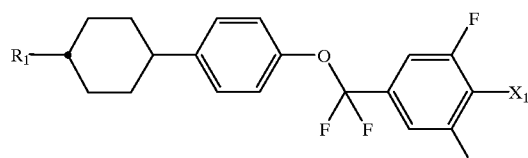
(3-43)
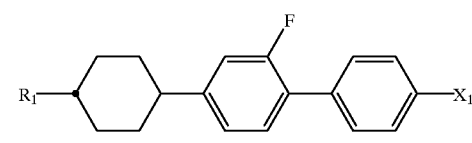
(3-44)
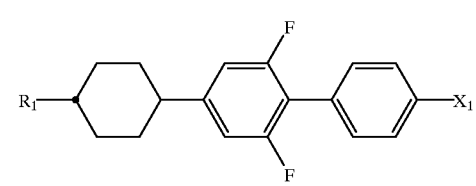
(3-45)
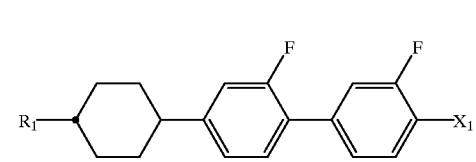
(3-46)
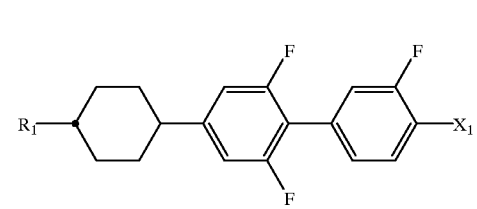
(3-47)
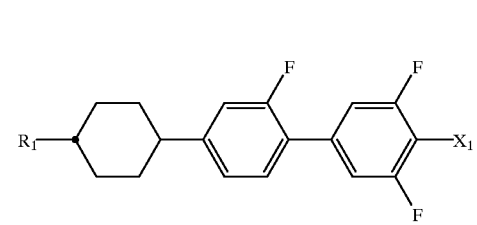
(3-48)
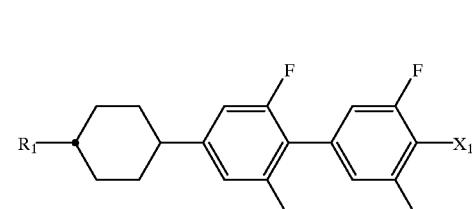
(3-49)
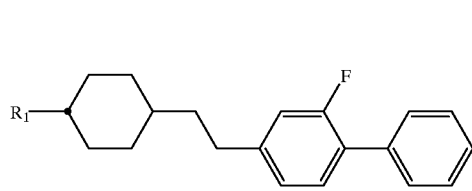
(3-50)
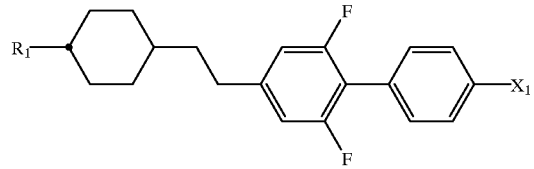
(3-51)
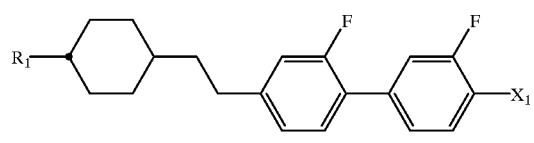
(3-52)
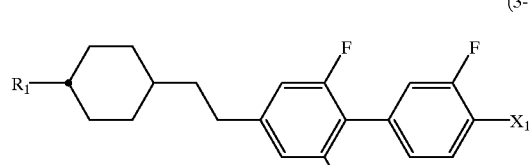
(3-53)
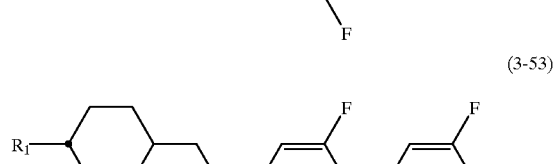
(3-54)
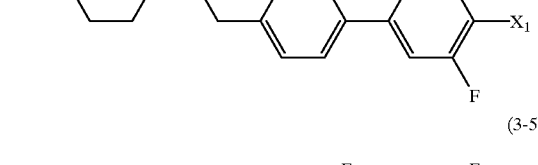
(3-55)
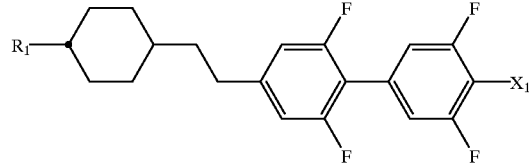
(3-56)
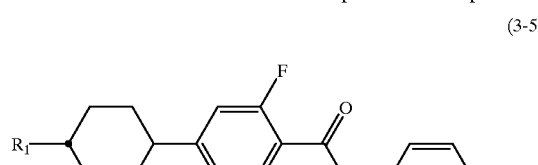
(3-57)
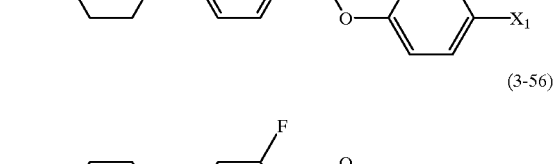

(3-58)
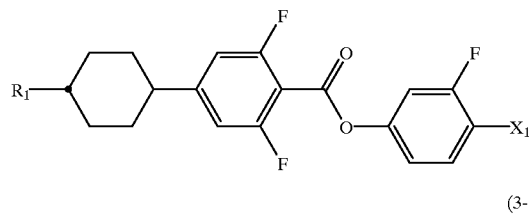
(3-59)
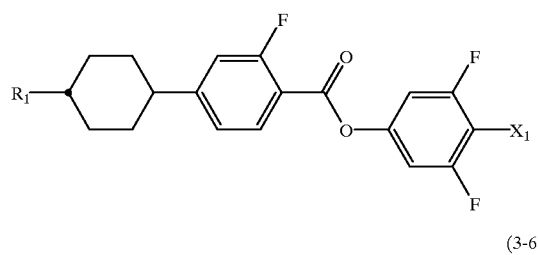
(3-60)
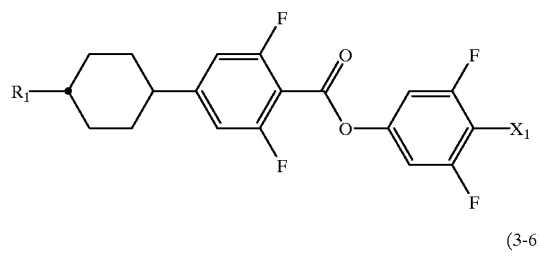
(3-61)
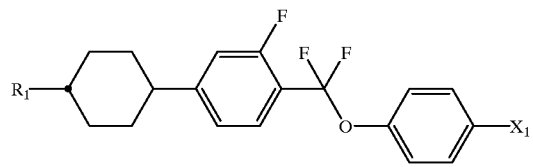
(3-62)
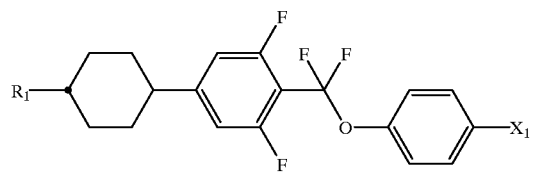
(3-63)
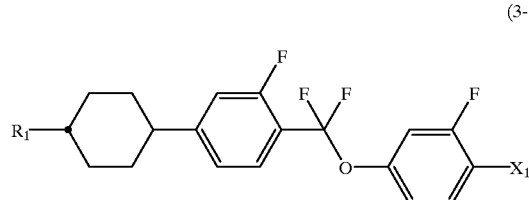
(3-64)
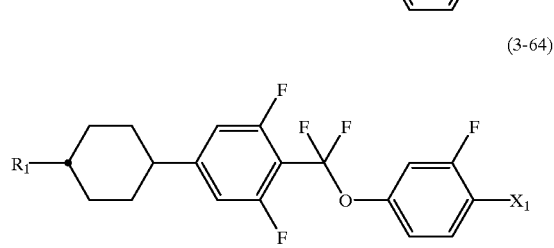
(3-65)
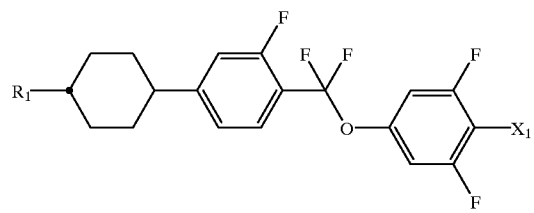
(3-66)
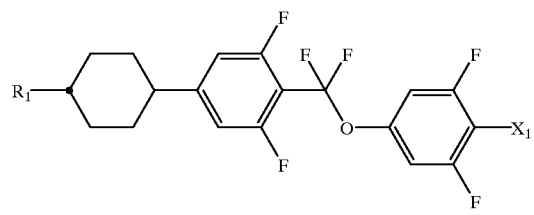
(3-67)
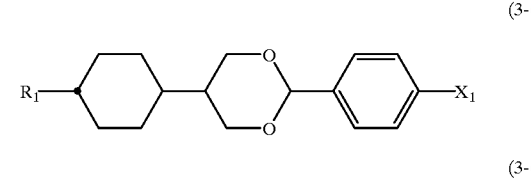
(3-68)
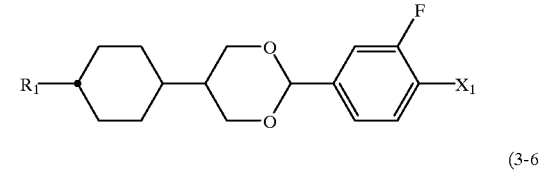
(3-69)
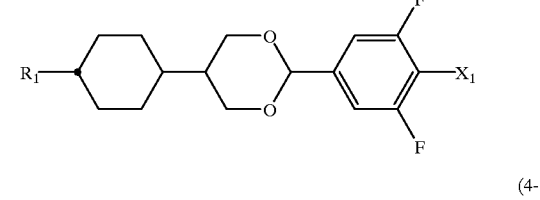
(4-1)
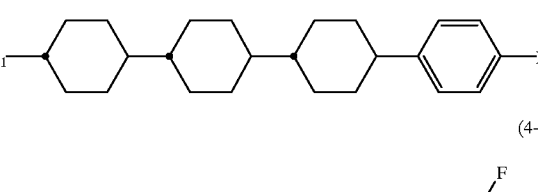
(4-2)
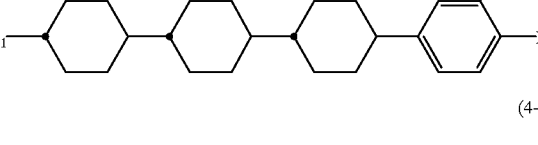
(4-3)
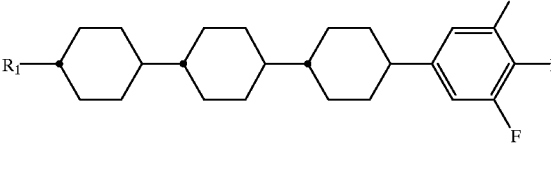

(4-4)
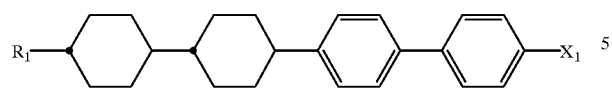
(4-5)
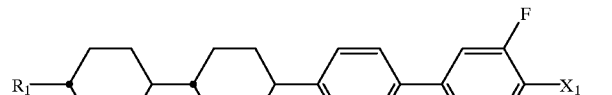
(4-6)
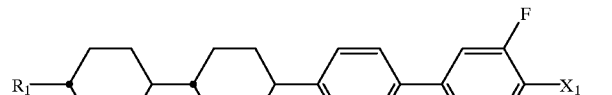
(4-7)
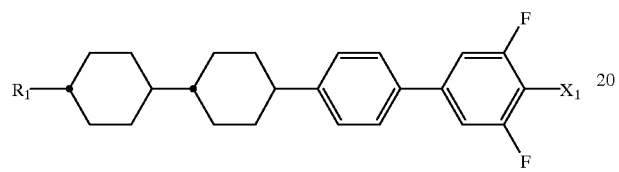
(4-8)
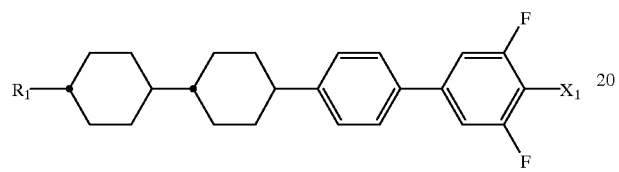
(4-9)
(4-10)
(4-11)
(4-12)
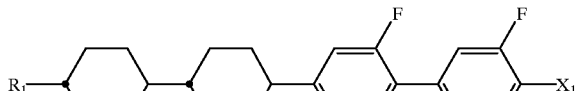
(4-13)
(4-14)
(4-15)
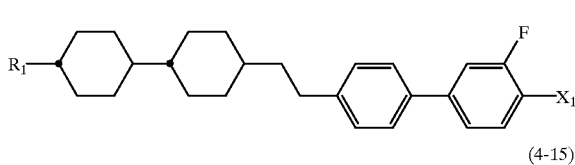
(4-16)
(4-17)
(4-18)
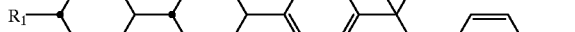
(4-19)
(4-20)

-continued (4-21)
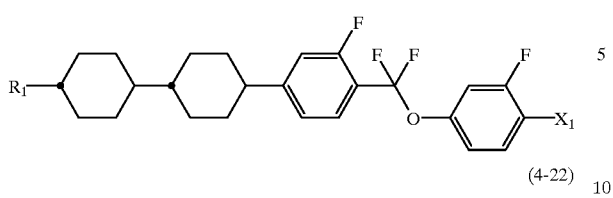

(4-22)
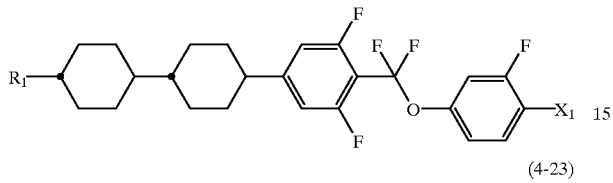

(4-23)
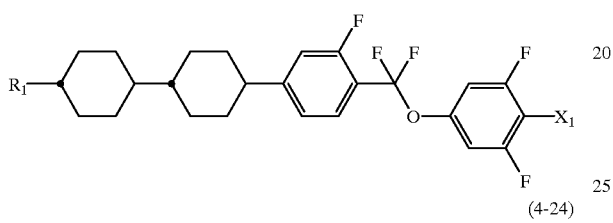

(4-24)
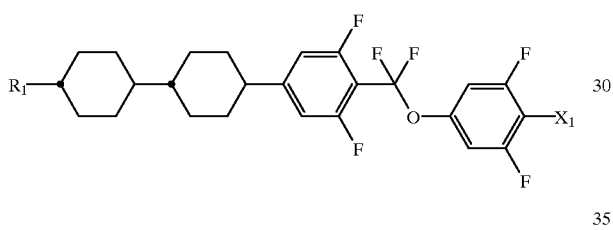

wherein $R_1$ and $X_1$ have the same meaning as described above.

Compounds expressed by one of the general formulas (2) to (4) have a positive dielectric anisotropy value, are remarkably excellent in thermal stability and chemical stability, and thus are extremely useful when liquid crystal compositions for TFT, of which a high reliability particularly such as a high voltage holding ratio or high specific resistance is required, are produced.

When the liquid crystal compositions for TFT are produced, the compound expressed by one of the general formulas (2) to (4) can be used in the range of 0.1 to 99.9% by weight based on the total amount of liquid crystal composition, and the amount is preferably 10 to 97% by weight and more desirably 40 to 95% by weight. The liquid crystal compositions may further comprise a compound expressed by one of the general formulas (7) to (9) for the purpose of adjusting viscosity.

Also, when liquid crystal compositions for STN or TNT are produced, the compound expressed by one of the general formulas (2) to (4) can be used, but the amount is preferably 50% by weight or less.

As preferable examples of the compounds used for the liquid crystal compositions of the present invention and expressed by the general formula (5) or (6), the following compounds can be mentioned:

(5-1)
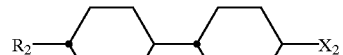

(5-2)
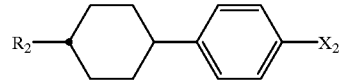

(5-3)
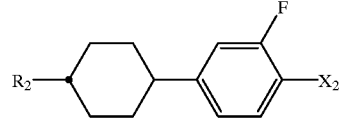

(5-4)
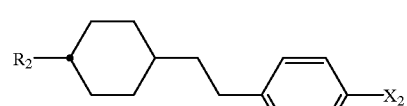

(5-5)
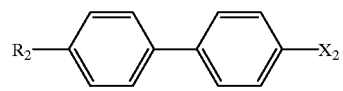

(5-6)
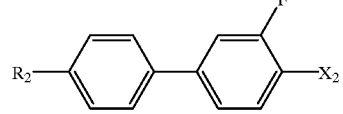

(5-7)
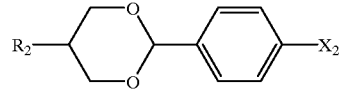

(5-8)
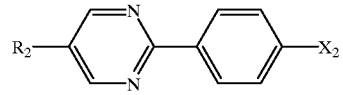

(5-9)
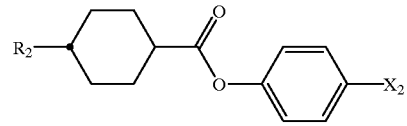

(5-10)
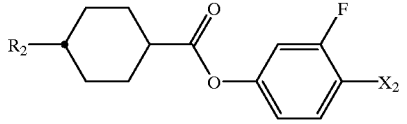

(5-11)
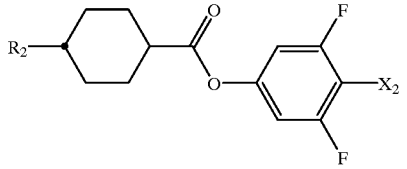

(5-12) 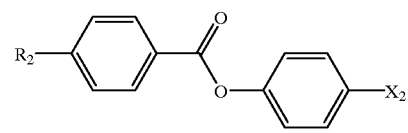
(5-13) 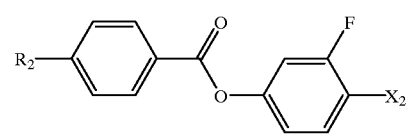
(5-14) 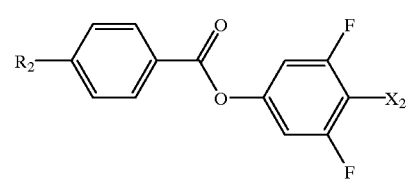
(5-15) 
(5-16) 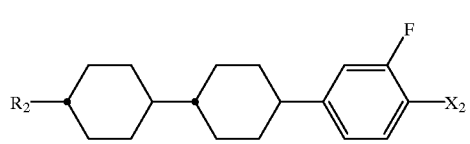
(5-17) 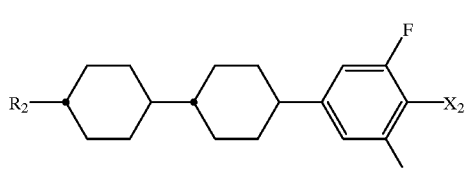
(5-18) 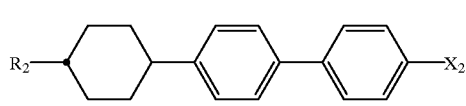
(5-19) 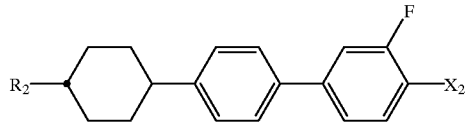
(5-20) 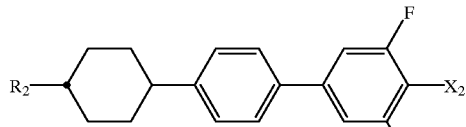
(5-21) 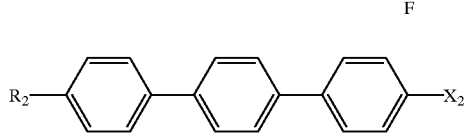
(5-22) 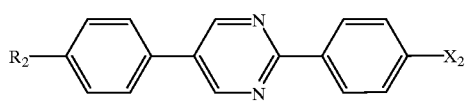
(5-23) 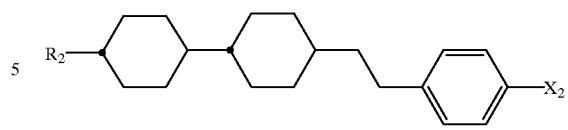
(5-24) 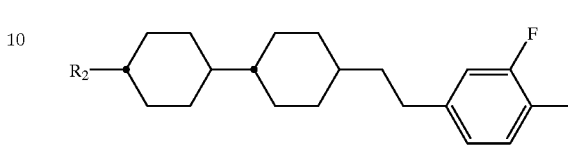
(5-25) 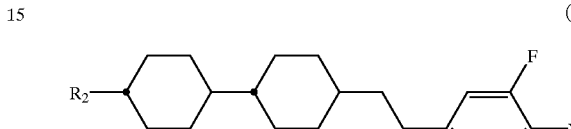
(5-26) 
(5-27) 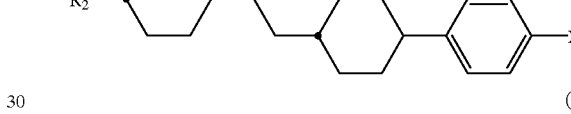
(5-28) 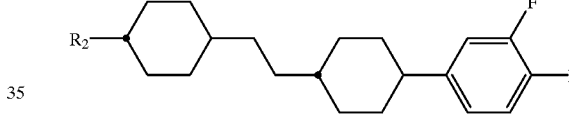
(5-29) 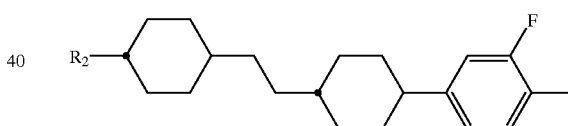
(5-30) 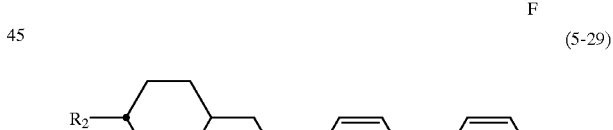
(5-31) 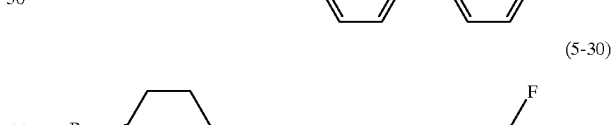

(5-32) 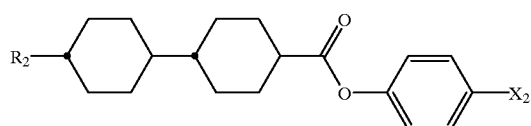

(5-33) 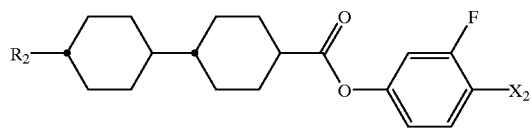

(5-34) 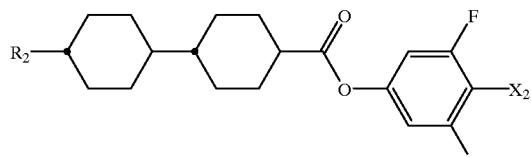

(5-35) 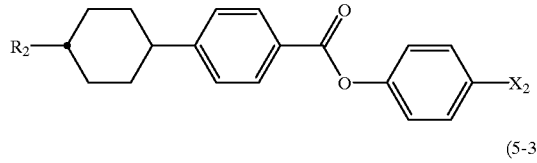

(5-36) 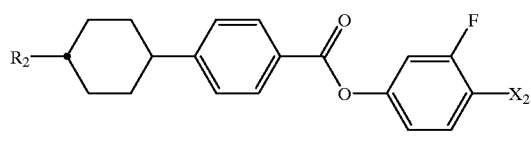

(5-37) 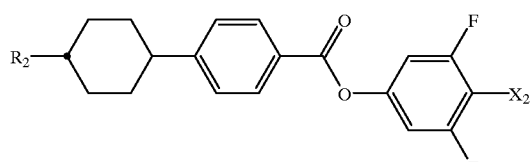

(5-38) 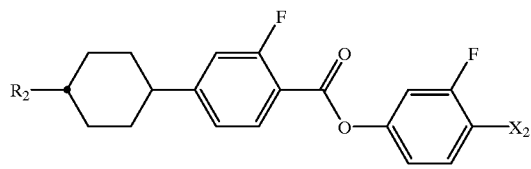

(5-39) 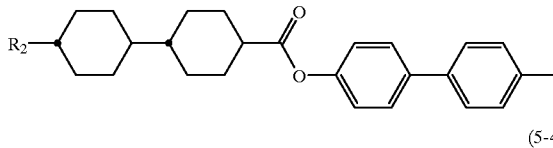

(5-40) 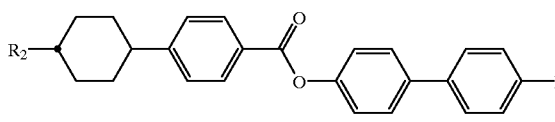

(6-1) 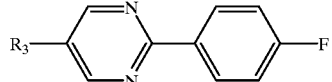

(6-2) 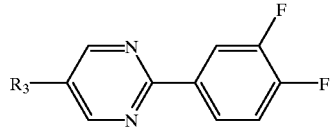

(6-3) 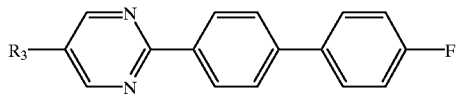

wherein $R_2$, $R_3$ and $X_2$ have the same meaning as described above.

Compounds expressed by the general formula (5) or (6) have a positive and high dielectric anisotropy value and are used particularly for the purpose of lowering the threshold voltage of liquid crystal compositions. The compounds are also used for the purpose of adjusting optical anisotropy value and expanding nematic range such as raising clearing point. Further, the compounds are used for the purpose of improving the steepness in the voltage-transmittance characteristic of liquid crystal compositions for STN or TN.

Compounds expressed by the general formula (5) or (6) are particularly useful when liquid crystal compositions for STN or TN are produced.

When the amount of the compound expressed by the general formula (5) or (6) is increased in the liquid crystal compositions, the threshold voltage of the liquid crystal compositions is lowered, but the viscosity is increased. Accordingly, it is advantageous to use a large amount of the compound since the compositions can be driven at a low voltage, so far as the viscosity of liquid crystal compositions satisfies a required value.

When the liquid crystal compositions for STN or TN are produced, the compound expressed by the general formula (5) or (6) can be used in the range of 0.1 to 99.9% by weight, and the amount is preferably 10 to 97% by weight and more desirably 40 to 95% by weight.

As preferable examples of the compounds used for the liquid crystal compositions of the present invention and expressed by one of the general formulas (7) to (9), the following compounds can be mentioned:

(7-1) 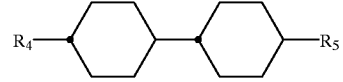

(7-2) 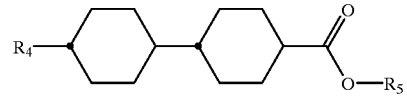

(7-3) 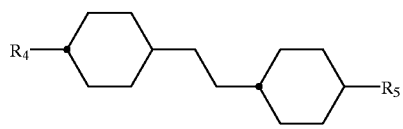
(7-4) 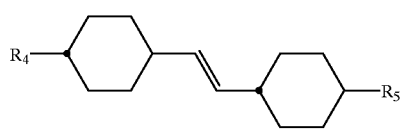
(7-5) 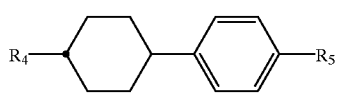
(7-6) 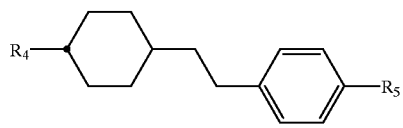
(7-7) 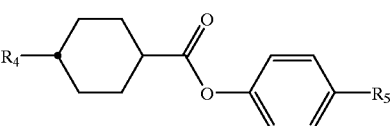
(7-8) 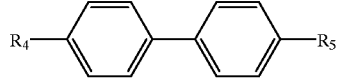
(7-9) 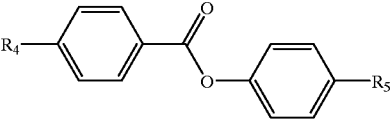
(7-10) 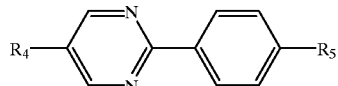
(7-11) 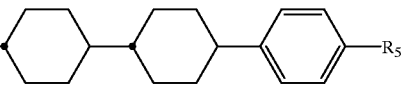
(8-1) 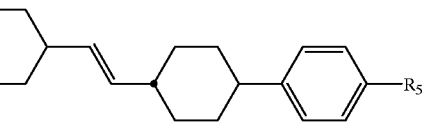
(8-2) 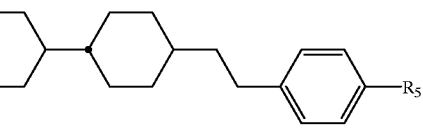
(8-3) 
(8-4) 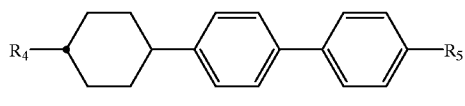
(8-5) 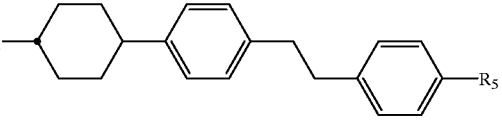
(8-6) 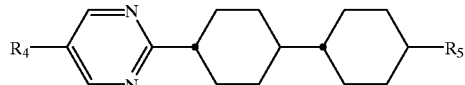
(8-7) 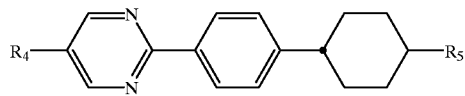
(8-8) 
(8-9) 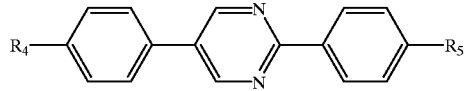
(8-10) 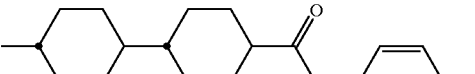
(8-11) 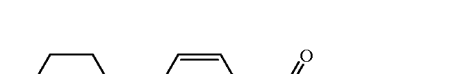
(8-12) 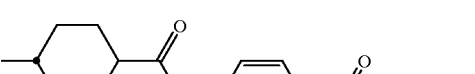
(8-13) 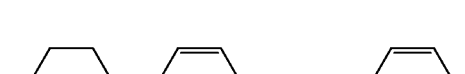
(8-14) 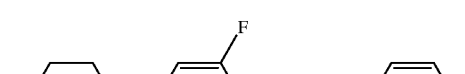

-continued (8-15)
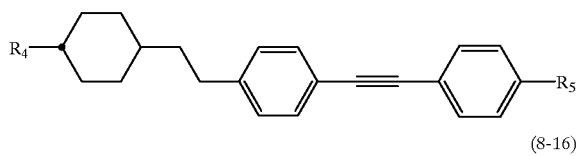

(8-16)
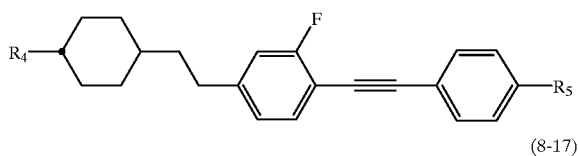

(8-17)
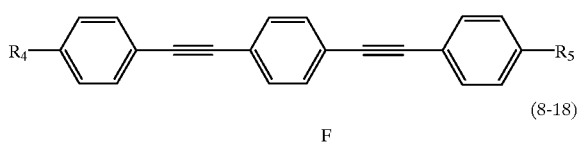

(8-18)
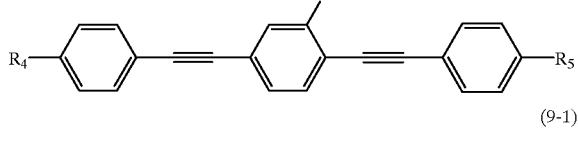

(9-1)
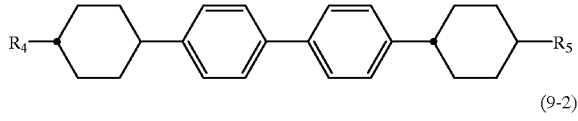

(9-2)
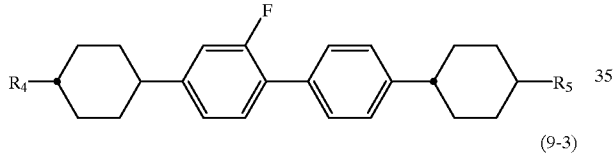

(9-3)
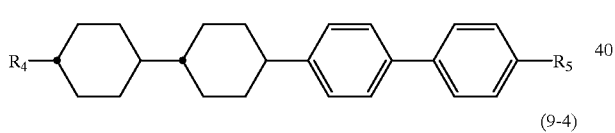

(9-4)
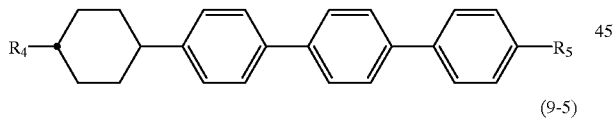

(9-5)
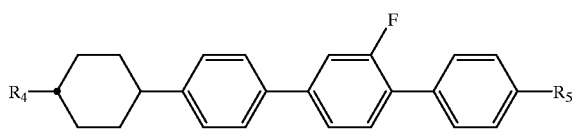

(9-6)
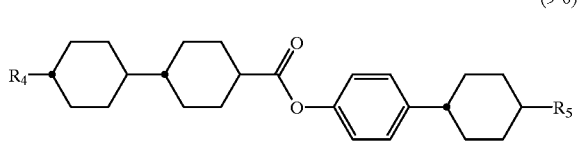

wherein $R_4$ and $R_5$ have the same meaning as described above.

Compounds expressed by one of the general formulas (7) to (9) have a small absolute value of dielectric anisotropy and are close to neutral. Compounds expressed by the general formula (7) are used principally for the purpose of adjusting viscosity or adjusting optical anisotropy value. Compounds expressed by the general formula (8) or (9) are used for the purpose of expanding nematic range such as raising clearing point or for the purpose of adjusting optical anisotropy value.

When the amount of the compounds expressed by one of the general formulas (7) to (9) to be used is increased, the threshold voltage of liquid crystal compositions rises and the viscosity lowers. Accordingly, it is desirable to use a large amount of the compounds so far as liquid crystal compositions satisfy a required value of threshold voltage. When liquid crystal compositions for TFT are produced, the amount of the compound expressed by one of the general formulas (7) to (9) to be used is preferably 40% by weight or less and more preferably 35% by weight or less. When liquid crystal compositions for STN or TN are produced, the amount of the compounds expressed by one of the general formulas (7) to (9) to be used is preferably 70% by weight or less and more preferably 60% by weight or less.

As preferable examples of the compounds used for the liquid crystal compositions of the present invention and expressed by one of the general formulas (10) to (12), the following compounds can be mentioned:

(10-1)
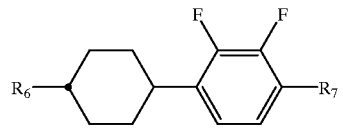

(10-2)
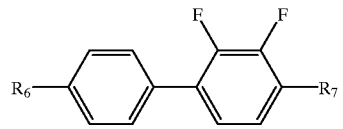

(10-3)
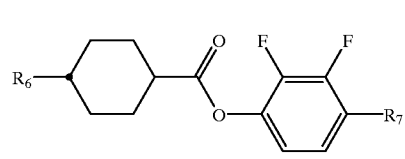

(11-1)
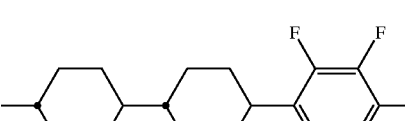

(11-2)
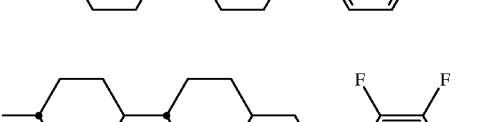

(11-3)
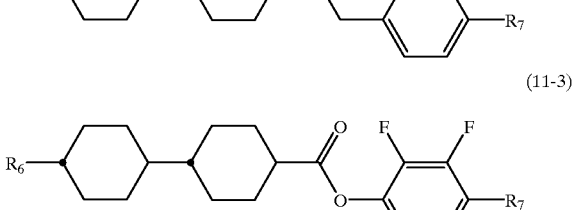

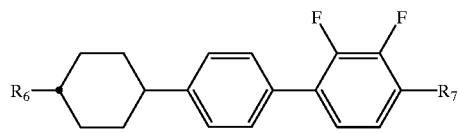
(11-4)

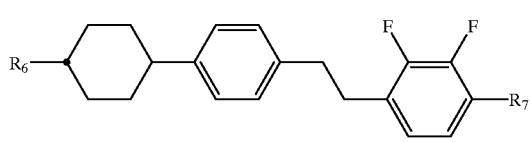
(11-5)

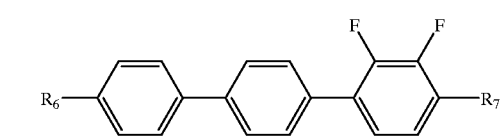
(12-1)

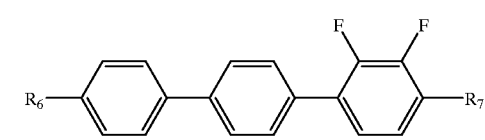
(12-2)

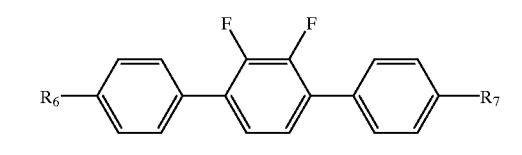
(12-3)

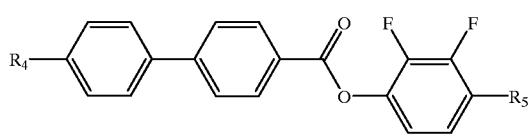

wherein $R_6$ and $R_7$ have the same meaning as described above.

Compounds expressed by one of the general formulas (10) to (12) have a negative dielectric anisotropy value. Since the compounds expressed by the general formula (10) are two rings compounds, the compounds are used principally for the purpose of adjusting threshold voltage, adjusting viscosity, or adjusting optical anisotropy value. Compounds expressed by the general formula (11) are used for the purpose of expanding nematic range such as raising clearing point or for the purpose of adjusting optical anisotropy value. Compounds expressed by the general formula (12) are used for the purpose of lowering threshold voltage and for the purpose of increasing optical anisotropy value in addition to the purpose of expanding nematic range.

Compounds expressed by one of the general formulas (10) to (12) are used principally for liquid crystal compositions having a negative dielectric anisotropy value. When the amount of the compounds to be used is increased, the threshold voltage of liquid crystal compositions lowers but the viscosity increases. Accordingly, it is desirable to use a small amount of the compounds so far as the liquid crystal compositions satisfy a required threshold voltage value. However, when the amount becomes less than 40% by weight, in some cases, it becomes impossible to drive liquid crystal compositions at a low voltage since the absolute value of dielectric anisotropy is 5 or lower. The amount of the compound expressed by one of the general formulas (10) to (12) to be used is preferably 40% by weight or more, and more preferably 50 to 95% by weight when liquid crystal compositions used for TFT and having a negative dielectric anisotropy value are produced. Sometimes, the compounds expressed by one of the general formulas (10) to (12) are mixed with liquid crystal compositions having a positive dielectric anisotropy for the purpose of controlling elastic constant and controlling voltage-transmittance characteristic. In this case, the amount of the compounds expressed by one of the general formulas (10) to (12) to be used is preferably 30% by weight or less.

Except for specific cases of liquid crystal compositions for OCB (Optically Compensated Birefringence) mode or the likes, an optically active compound is usually added in the liquid crystal compositions of the present invention for the purpose of inducing a helical structure of liquid crystal composition to adjust a required twisting angle and to avoid a reverse-twist. Any known optically active compounds can be used for such purpose, and the following optically active compounds can be mentioned as preferable examples:

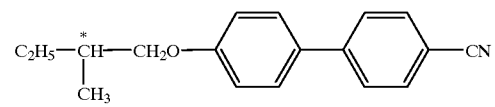
Symbol: C15

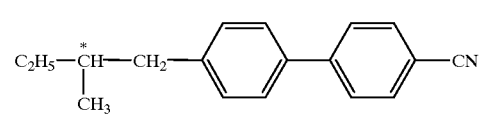
Symbol: CB15

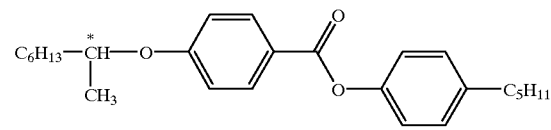
Symbol: CM21

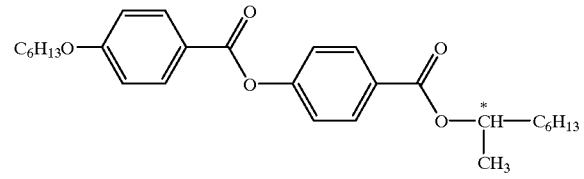
Symbol: CM33

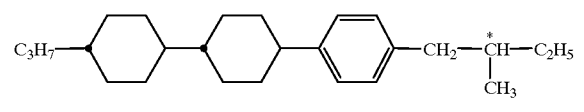
Symbol: CM43L

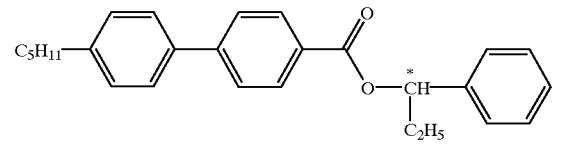
Symbol: CM45

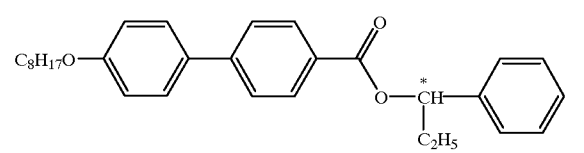
Symbol: CM47

Symbol: CN

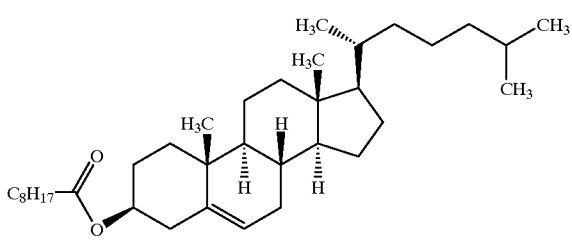

In the liquid crystal compositions of the present invention, the pitch in the twist of liquid crystals is usually adjusted by adding these optically active compounds. The twist pitch is preferably adjusted in the range of 40 to 200 µm in the case of liquid crystal compositions for TFT or TN. In the case of liquid crystal compositions for STN, it is preferable to adjust the twist pitch in the range of 6 to 20 µm. In the case of the liquid crystal compositions for bistable TN mode, it is preferable to adjust the twist pitch in the range of 1.5 to 4 µm. Further, two or more kind of optically active compounds may be added for the purpose of adjusting the dependency of the pitch on temperature.

Liquid crystal compositions of the present invention can be produced by conventional methods. Generally, methods wherein various components are dissolved in each other at a high temperature are adopted.

Liquid crystal compositions of the present invention can be used as ones for guest-host (GH) mode by adding a dichroic dye such as merocyanine type, styryl type, azo type, azomethine type, azoxy type, quinophthalone type, anthraquinone type, or tetrazine type dye. Alternatively, the liquid crystal compositions of the present invention can also be used as ones for NCAP which is prepared by the microencapsulation of a nematic liquid crystal, or for polymer dispersed liquid crystal display devices (PDLCD) represented by polymer network liquid crystal display device (PNLCD) prepared by forming polymers of three-dimensional reticulated structure in a liquid crystal. In addition, the liquid crystal compositions of the present invention can be used as ones for electrically controlled birefringence (ECB) mode or dynamic scattering (DS) mode.

As examples of the liquid crystal compositions comprising the liquid crystalline compound of the present invention, the following Composition Examples can be mentioned. Compound in the Composition Examples and Examples described below are designated by using symbols according to the definitions shown in the Tables below. Compound numbers shown in the Composition Examples are the same as those shown in Examples described below.

| Left side terminal group Ra, $R_1 \sim R_4$, $R_6$ | Symbol |
|---|---|
| $C_aH_{2a+1}$— | a- |
| $C_aH_{2a+1}O$— | aO- |
| $C_aH_{2a+1}OC_bH_{2b}$— | aOb- |
| $C_aH_{2a+1}OC_bH_{2b}O$— | aObO- |
| $C_{a-1}H_{2(a-1)+1}C(C_bH_{2b+1})HC_cH_{2c}$— | a(b)c- |
| $CFH_2C_{a-1}H_{2(a-1)}$— | Fa- |
| $CF_2HC_{a-1}H_{2(a-1)}$— | FFa- |
| $CF_3C_{a-1}H_{2(a-1)}$— | FFFa- |
| $CFH_2C_{a-1}H_{2(a-1)}O$— | FaO- |

| Left side terminal group Ra, $R_1 \sim R_4$, $R_6$ | Symbol |
|---|---|
| $CFH_2C_{a-1}H_{2(a-1)}OC_bH_{2b}$— | FaOb- |
| $C_aH_{2a+1}CFHC_bH_{2b}$— | a(F)b- |
| $C_aH_{2a+1}CF_2C_bH_{2b}$— | a(FF)b- |
| $C_aH_{2a+1}SiH_2C_bH_{2b}$— | a(Si)b- |
| $C_aH_{2a+1}CH = CHC_bH_{2b}$— | aVb- |
| $C_aH_{2a+1}CH = CHC_bH_{2b}CH = CHC_cH_{2c}$— | aVbVc- |
| $C_aH_{2a+1}CH = CHC_bH_{2b}OC_cH_{2c}$— | aVbOc- |
| $C_aH_{2a+1}OC_bH_{2b}CH = CHC_cH_{2c}$— | aObVc- |
| $CFH_2C_{a-1}H_{2(a-1)}CH = CHC_bH_{2b}$— | FaVb- |
| $FFC = CHC_aH_{2a}$— | FFVa- |
| $F(CN)C = CHC_aH_{2a}$— | FCVa- |
| Bonding group $Z_1 \sim Z_{10}$ | |
| —$(CH_2)_a$— | a |
| —$CH_2O$— | $CH_2O$ |
| —$OCH_2$— | $OCH_2$ |
| —$C_3H_6O$— | $C_3H_6O$ |
| —$OC_3H_6$— | $OC_3H_6$ |
| —COO— | E |
| —C≡C— | T |
| —CH=CH— | V |
| —$CF_2O$— | $CF_2O$ |
| —$OCF_2$— | $OCF_2$ |

| Ring structure | |
|---|---|
| Ring B~Ring M | Symbol |
| (benzene ring) | B |
| (2-fluorobenzene) | B(2F) |
| (3-fluorobenzene) | B(3F) |
| (2-chlorobenzene) | B(2Cl) |
| (3-chlorobenzene) | B(3Cl) |
| (2,3-difluorobenzene) | B(2,3F) |

-continued

| Ring structure | |
|---|---|
| [2,3-dichlorophenylene] | B(2,3Cl) |
| [2,3-dicyanophenylene] | B(2,3C) |
| [2-F,3-Cl phenylene] | B(2F,3Cl) |
| [2-Cl,3-F phenylene] | B(2Cl,3F) |
| [3,5-difluorophenylene] | B(3,5F) |
| [3-F,5-Cl phenylene] | B(3F,5Cl) |
| [trans-cyclohexylene] | H |
| [cyclohexenylene] | Ch |
| [tetrahydropyran-2,5-diyl] | P(2) |
| [tetrahydropyran-3,2-diyl] | P(3) |
| [1,3-dioxane-2,5-diyl] | D(2,5) |

-continued

| Ring structure | |
|---|---|
| [1,3-dioxane-2,5-diyl isomer] | D(1,6) |
| [1,3-dioxane-3,5-diyl isomer] | D(3,5) |
| [silacyclohexane] | Si(1) |
| [silacyclohexane isomer] | Si(4) |
| [pyrimidine-2,5-diyl] | Py(1,6) |
| [pyrimidine-2,5-diyl isomer] | Py(2,5) |
| [pyridine-2,5-diyl] | Pr(2) |
| [pyridine-2,5-diyl isomer] | Pr(3) |
| [2-fluoropyridine-3,6-diyl] | Pr(3F) |

| Right side terminal group Rb, R$_5$, R$_7$, X$_1$, X$_2$ | Symbol |
|---|---|
| —F | —F |
| —Cl | —CL |
| —CN | —C |
| —CF$_3$ | —CF$_3$ |
| —OCF$_3$ | —OCF$_3$ |
| —OCF$_2$H | —OCF$_2$H |
| —CF$_2$CF$_2$H | —CF$_2$CF$_2$H |
| —CF$_2$CH$_2$CF$_3$ | —CF$_2$CH$_2$CF$_3$ |
| —CF$_2$CFHCF$_3$ | —CF$_2$CFHCF$_3$ |
| —OCH$_2$CF$_2$H | —OCH$_2$CF$_2$H |
| —OCF$_2$CF$_2$H | —OCF$_2$CF$_2$H |
| —OCF$_2$CH$_2$CF$_3$ | —OCF$_2$CH$_2$CF$_3$ |
| —OCF$_2$CFHCF$_3$ | —OCF$_2$CFHCF$_3$ |
| —C$_w$H$_{2w+1}$ | -w |
| —OC$_w$H$_{2w+1}$ | —Ow |
| —C$_w$H$_{2w}$OC$_x$H$_{2x+1}$ | -wOx |

-continued

| Right side terminal group Rb, R$_5$, R$_7$, X$_1$, X$_2$ | Symbol |
|---|---|
| —OC$_w$H$_{2w}$OC$_x$H$_{2x+1}$ | —OwOx |
| —C$_{w-1}$H$_{2(w-1)}$CFH$_2$ | -wF |
| —C$_w$H$_{2w}$CH = CH$_2$ | -wV |
| —C$_w$H$_{2w}$CH = CHC$_x$H$_{2x+1}$ | -wVx |
| —C$_w$H$_{2w}$CH = CHC$_x$H$_{2x}$CH = CH$_2$ | -wVxV |
| —COOCH$_3$ | -EMe |
| —C$_w$H$_{2w}$CH = CHC$_{x-1}$H$_{2(x-1)}$CFH$_2$ | -wVxF |
| —CH = CF$_2$ | -VFF |
| —C$_w$H$_{2w}$CH = CF$_2$ | -wVFF |
| —C≡C—CN | -TC |

Further, when hydrogen atom of trans-1,4-cyclohexylene, for example, in the following partial structural formulas is replaced by deuterium atom at positions Q$_1$, Q$_2$, and Q$_3$, it is represented by symbol: H[1D, 2D, 3D]; when the hydrogen atom is replaced at positions Q$_5$, Q$_6$ and Q$_7$, it is represented by symbol: H[5D, 6D, 7D]; and thus, the position where hydrogen atom is replaced by deuterium atom is indicated by the numeral in the brackets.

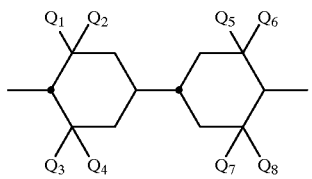

In the following Composition Examples and Examples, % means percent by weight unless otherwise indicated, and when cis and trans isomers exist for a compound, the compound is trans form.

| Composition Example 1 | | |
|---|---|---|
| 2O-B(2,3F)B(3F)2B-3 | (Compound No. 1) | 15.0% |
| 3-HEB-O4 | | 24.0% |
| 4-HEB-O2 | | 17.0% |
| 5-HEB-O1 | | 17.0% |
| 3-HEB-O2 | | 15.0% |
| 5-HEB-O2 | | 12.0% |
| Composition Example 2 | | |
| 2-BB(2,3F)2B(2,3F)-3 | (Compound No. 62) | 15.0% |
| 3-HEB-O4 | | 24.0% |
| 4-HEB-O2 | | 17.0% |
| 5-HEB-O1 | | 17.0% |
| 3-HEB-O2 | | 15.0% |
| 5-HEB-O2 | | 12.0% |
| Composition Example 3 | | |
| 2-BB(2F)2B(2,3F)-3 | (Compound No. 50) | 8.0% |
| 2-BB(2,3F)2B(2,3F)-3 | (Compound No. 62) | 2.0% |
| 3-HH-2 | | 5.0% |
| 3-HH-4 | | 6.0% |
| 3-HH-O1 | | 4.0% |
| 3-HH-O3 | | 5.0% |
| 5-HH-O1 | | 4.0% |
| 3-HB(2,3F)-O2 | | 12.0% |
| 5-HB(2,3F)-O2 | | 11.0% |
| 3-HHB(2,3F)-O2 | | 14.0% |
| 5-HHB(2,3F)-O2 | | 15.0% |
| 3-HHB(2,3F)-2 | | 14.0% |
| Composition Example 4 | | |
| 2O-B(2,3F)B(3F)2B-3 | (Compound No. 1) | 12.0% |
| 2-BB(2F)2B(2,3F)-3 | (Compound No. 50) | 12.0% |
| 2-BB(2,3F)2B(2,3F)-3 | (Compound No. 62) | 12.0% |
| 3-HH-4 | | 3.0% |
| 3-HH-O1 | | 4.0% |
| 3-HH-O3 | | 4.0% |
| 3-HB-O1 | | 10.0% |
| 3-HB-O2 | | 5.0% |
| 3-HB(2,3F)-O2 | | 10.0% |
| 3-HHB(2,3F)-O2 | | 5.0% |
| 3-HHB(2,3F)-2 | | 4.0% |
| 2-HHB(2,3F)-1 | | 4.0% |
| 3-HHEH-3 | | 5.0% |
| 3-HHEH-5 | | 5.0% |
| 4-HHEH-3 | | 5.0% |
| Composition Example 5 | | |
| 2-BB(2F)2B(2,3F)-3 | (Compound No. 50) | 2.0% |
| 2-BB(2,3F)2B(2,3F)-3 | (Compound No. 62) | 5.0% |
| 3-BB(2,3F)-O2 | | 2.0% |
| 3-BB(2,3F)-O4 | | 10.0% |
| 5-BB(2,3F)-O4 | | 3.0% |
| 2-BB(2,3F)B-3 | | 25.0% |
| 3-BB(2,3F)B-5 | | 13.0% |
| 5-BB(2,3F)B-5 | | 14.0% |
| 5-BB(2,3F)B-7 | | 16.0% |
| Composition Example 6 | | |
| 2O-B(2,3F)B(3F)2B-3 | (Compound No. 1) | 5.0% |
| 2O-B(2F)B(2,3F)OCH$_2$B-3 | (Compound No. 163) | 5.0% |
| 3-BB(2,3F)-O2 | | 10.0% |
| 5-BB-5 | | 9.0% |
| 5-BB-O6 | | 9.0% |
| 5-BB-O8 | | 4.0% |
| 1-BEB-5 | | 6.0% |
| 5-BEB-5 | | 3.0% |
| 3-HEB-O2 | | 20.0% |
| 5-BBB(2,3F)-7 | | 9.0% |
| 3-H2BB(2F)-5 | | 20.0% |
| Composition Example 7 | | |
| 2O-B(2,3F)B(3F)2B-3 | (Compound No. 1) | 10.0% |
| 2-BB(2F)2B(2,3F)-3 | (Compound No. 50) | 2.0% |
| 3-HB-O1 | | 15.0% |
| 3-HB-O2 | | 6.0% |
| 3-HEB(2,3F)-O2 | | 9.0% |
| 4-HEB(2,3F)-O2 | | 9.0% |
| 5-HEB(2,3F)-O2 | | 9.0% |
| 2-BB2B-O2 | | 6.0% |
| 3-BB2B-O2 | | 6.0% |
| 1-B2BB(2F)-5 | | 7.0% |
| 3-B2BB(2F)-5 | | 7.0% |
| 5-B(3F)BB-O2 | | 7.0% |
| 3-BB(2,3F)B-3 | | 7.0% |
| Composition Example 8 | | |
| 2-BB(2F)2B(2,3F)-3 | (Compound No. 50) | 3.0% |
| 2-BB(2,3F)2B(2,3F)-3 | (Compound No. 62) | 2.0% |
| 3-HB-O1 | | 9.0% |
| 3-HB-O2 | | 9.0% |
| 3-HB-O4 | | 9.0% |
| 2-BTB-O1 | | 5.0% |
| 3-BTB(2,3F)-O2 | | 13.0% |
| 5-BTB(2,3F)-O2 | | 13.0% |
| 3-B(2,3F)TB(2,3F)-O4 | | 4.0% |
| 5-B(2,3F)TB(2,3F)-O4 | | 4.0% |
| 3-HBTB-O1 | | 5.0% |
| 3-HBTB-O2 | | 5.0% |
| 3-HBTB-O3 | | 5.0% |
| 3-HHB(2,3F)-O2 | | 6.0% |
| 5-HHB(2,3F)-O2 | | 5.0% |
| 5-BPr(3F)-O2 | | 3.0% |
| Composition Example 9 | | |
| 2O-B(2,3F)B(3F)2B-3 | (Compound No. 1) | 5.0% |
| 2-BB(2F)2B(2,3F)-3 | (Compound No. 50) | 5.0% |
| 3-HB-O2 | | 10.0% |
| 5-HB-3 | | 8.0% |
| 5-BB(2,3F)-O2 | | 10.0% |
| 3-HB(2,3F)-O2 | | 10.0% |
| 5-HB(2,3F)-O2 | | 3.0% |

| | | |
|---|---|---|
| 3-HHB(2,3F)-O2 | | 12.0% |
| 5-HHB(2,3F)-O2 | | 4.0% |
| 5-HHB(2,3F)-1O1 | | 4.0% |
| 2-HHB(2,3F)-1 | | 5.0% |
| 3-HHB(2,3F)-1 | | 5.0% |
| 3-HBB-2 | | 6.0% |
| 3-BB(2,3F)B-3 | | 8.0% |
| 5-B2BB(2,3F)B-O2 | | 5.0% |
| Composition Example 10 | | |
| | | |
| 2O-B(2,3F)B(3F)2B-3 | (Compound No. 1) | 7.0% |
| 3-HB-O2 | | 20.0% |
| 1O1-HH-3 | | 6.0% |
| 3-HH-EMe | | 10.0% |
| 4-HEB-O1 | | 9.0% |
| 4-HEB-O2 | | 7.0% |
| 5-HEB-O1 | | 8.0% |
| 3-HHB-1 | | 6.0% |
| 3-HHB-3 | | 6.0% |
| 4-HEB(2,3C)-O4 | | 3.0% |
| 6-HEB(2,3C)-O4 | | 3.0% |
| 3-HEB(2,3C)-O5 | | 4.0% |
| 4-HEB(2,3C)-O5 | | 3.0% |
| 5-HEB(2,3C)-O5 | | 2.0% |
| 2-HBEB(2,3C)-O2 | | 2.0% |
| 4-HBEB(2,3C)-O4 | | 4.0% |
| Composition Example 11 | | |
| | | |
| 2O-B(2,3F)B(3F)2B-3 | (Compound No. 1) | 5.0% |
| 2-BB(2F)2B(2,3F)-3 | (Compound No. 50) | 5.0% |
| 2-BB(2,3F)2B(2,3F)-3 | (Compound No. 62) | 5.0% |
| 1V2-BEB(3,5F)-C | | 5.0% |
| V2-HB-C | | 6.0% |
| 1-BTB-3 | | 5.0% |
| 1O1-HH-3 | | 3.0% |
| 3-HH-4 | | 6.0% |
| 3-HHB-1 | | 11.0% |
| 3-HHB-3 | | 3.0% |
| 3-H2BTB-2 | | 4.0% |
| 3-H2BTB-3 | | 4.0% |
| 3-H2BTB-4 | | 4.0% |
| 3-HB(3F)TB-2 | | 6.0% |
| 3-HB(3F)TB-3 | | 5.0% |
| 3-HHB-C | | 3.0% |
| Composition Example 12 | | |
| | | |
| 2O-B(2,3F)B(3F)2B-3 | (Compound No. 1 | 12.0% |
| 5-PYB-F | | 4.0% |
| 3-PYB(3F)-F | | 4.0% |
| 2-BB-C | | 5.0% |
| 4-BB-C | | 4.0% |
| 5-BB-C | | 5.0% |
| 2-PyB-2 | | 2.0% |
| 3-FyB-2 | | 2.0% |
| 4-PyB-2 | | 2.0% |
| 6-PyB-O5 | | 3.0% |
| 3-PYBB-F | | 6.0% |
| 4-PYBB-F | | 6.0% |
| 5-PyBB-F | | 6.0% |
| 3-HHB-1 | | 6.0% |
| 3-HHB-3 | | 5.0% |
| 2-H2BTB-2 | | 4.0% |
| 2-H2BTB-3 | | 4.0% |
| 2-H2BTB-4 | | 5.0% |
| 3-H2BTB-2 | | 5.0% |
| 3-H2BTB-3 | | 5.0% |
| 3-H2BTB-4 | | 5.0% |
| Composition Example 13 | | |
| | | |
| 2O-B(213F)B(3F)2B-3 | (Compound No. 1) | 5.0% |
| 2-BB(2F)2B(2,3F)-3 | (Compound No. 50) | 4.0% |
| 2O1-BEB(3F)-C | | 5.0% |
| 3O1-BEB (3F)-C | | 12.0% |
| 5O1-BEB(3F)-C | | 4.0% |
| 1V2-BEB(3,5F)-C | | 10.0% |
| 3-HEB-O4 | | 4.0% |
| 3-HH-EMe | | 6.0% |
| 3-HB-O2 | | 18.0% |
| 7-HEB-F | | 2.0% |
| 3-HHEB-F | | 2.0% |
| 5-HHEB-F | | 2.0% |
| 3-HBEB-F | | 4.0% |
| 2O1-HBEB(3F)-C | | 2.0% |
| 3-HB(3F)EB(3F)-C | | 2.0% |
| 3-HBEB(3,5F)-C | | 2.0% |
| 3-HHB-F | | 4.0% |
| 3-HHB-O1 | | 4.0% |
| 3-HEBEB-F | | 2.0% |
| 3-HEBEB-1 | | 2.0% |
| 3-HHB(3F)-C | | 4.0% |
| Composition Example 14 | | |
| | | |
| 2-BB(2F)2B(2,3F)-3 | (Compound No. 50) | 7.0% |
| 2-BB(2,3F)2B(2,3F)-3 | (Compound No. 62) | 3.0% |
| 5-BEB(3F)-C | | 5.0% |
| V-HB-C | | 11.0% |
| 5-PyB-C | | 6.0% |
| 4-BB-3 | | 4.0% |
| V2V-HH-5 | | 4.0% |
| 3-HH-2V | | 10.0% |
| 5-HH-V | | 7.0% |
| V-HHB-1 | | 7.0% |
| V2-HHB-1 | | 15.0% |
| 3-HHB-1 | | 6.0% |
| 1V2-HBB-2 | | 10.0% |
| 3-HHEBH-3 | | 5.0% |
| Composition Example 15 | | |
| | | |
| 2-BB(2F)2B(213F)-3 | (Compound No. 50) | 10.0% |
| 5-BTB(3F)TB-3 | | 10.0% |
| V2-HB-TC | | 10.0% |
| 3-HB-TC | | 10.0% |
| 3-HB-C | | 10.0% |
| 5-HB-C | | 7.0% |
| 5-BB-C | | 3.0% |
| 2-BTB-1 | | 2.0% |
| 2-BTB-O1 | | 5.0% |
| 3-HH-4 | | 5.0% |
| 3-HHB-1 | | 10.0% |
| 3-HHB-3 | | 9.0% |
| 3-H2BTB-2 | | 3.0% |
| 3-H2BTB-3 | | 3.0% |
| 3-HB(3F)TB-2 | | 3.0% |
| Composition Example 16 | | |
| | | |
| 2-BB(2,3F)2B(2,3F)-3 | (Compound No. 62) | 10.0% |
| 1V2-BEB(3,5F)-C | | 6.0% |
| 3-HB-C | | 18.0% |
| 2-BTB-1 | | 5.0% |
| 5-HH-VFF | | 27.0% |
| 1-BHH-VFF | | 8.0% |
| 1-BHH-2VFF | | 11.0% |
| 3-H2BTB-2 | | 5.0% |
| 3-H2BTB-3 | | 4.0% |
| 3-H2BTB-4 | | 4.0% |
| 3-HHB-1 | | 2.0% |
| Composition Example 17 | | |
| | | |
| 2-BB(2F)2B(2,3F)-3 | (Compound No. 50) | 8.0% |
| 7-HB(3F)-F | | 5.0% |
| 3-HB-O2 | | 10.0% |
| 3-HH-4 | | 2.0% |
| 3-HH[5D, 6D, 7D]-4 | | 3.0% |
| 2-HHB(3F)-F | | 10.0% |
| 3-HHB(3F)-F | | 10.0% |
| 5-HH[5D, 6D, 7D]B(3F)-F | | 10.0% |
| 3-H2HB(3F)-F | | 5.0% |
| 2-HBB(3F)-F | | 3.0% |
| 3-HBB(3F)-F | | 3.0% |
| 5-HBB(3F)-F | | 6.0% |
| 2-H2BB(3F)-F | | 3.0% |
| 3-HHB-1 | | 8.0% |
| 3-HHB-O1 | | 5.0% |
| 3-HHB-3 | | 4.0% |
| Composition Example 18 | | |
| | | |
| 2O-B(2,3F)B(3F)2B-3 | (Compound No. 1) | 8.0% |
| 2-BB(2,3F)2B(2,3F)-3 | (Compound No. 62) | 3.0% |

| | | |
|---|---|---|
| -continued | | |
| 2O-B(2F)B(2,3F)OCH₂B-3 | (Compound No. 163) | 3.0% |
| 7-HB(3,5F)-F | | 5.0% |
| 3-H2HB(3,5F)-F | | 12.0% |
| 4-H2HB(3,5F)-F | | 6.0% |
| 3-HHB(3,5F)-F | | 10.0% |
| 4-HHB(3,5F)-F | | 5.0% |
| 3-HBB(3,5F)-F | | 3.0% |
| 3-HHEB(3,5F)-F | | 10.0% |
| 4-HHEB(3,5F)-F | | 3.0% |
| 5-HHEB(3,5F)-F | | 3.0% |
| 2-HBEB(3,5F)-F | | 3.0% |
| 3-HBEB(3,5F)-F | | 5.0% |
| 5-HBEB(3,5F)-F | | 3.0% |
| 3-HD(3,5)B(3,5F)-F | | 8.0% |
| 3-HBCF₂OB-OCF₃ | | 4.0% |
| 3-HHBB(3,5F)-F | | 6.0% |
| Composition Example 19 | | |
| 2O-B(2,3F)B(3F)2B-3 | (Compound No. 1) | 5.0% |
| 2-BB(2F)2B(2,3F)-3 | (Compound No. 50) | 5.0% |
| 3-HB-CL | | 10.0% |
| 5-HB-CL | | 4.0% |
| 7-HB-CL | | 4.0% |
| 1O1-HH-5 | | 5.0% |
| 2-HBB(3F)-F | | 8.0% |
| 3-HBB(3F)-F | | 8.0% |
| 5-HBB(3F)-F | | 14.0% |
| 4-HHB-CL | | 8.0% |
| 5-HHB-CL | | 8.0% |
| 3-H2HB(3F)-CL | | 4.0% |
| 3-HBB(3,5F)-F | | 5.0% |
| 5-H2BB(3,5F)-F | | 4.0% |
| 3-HB(3F)VB-2 | | 4.0% |
| 3-H2BTB-2 | | 4.0% |
| Composition Example 20 | | |
| 2O-B(2,3F)B(3F)2B-3 | (Compound No. 1) | 8.0% |
| 2O-B(2F)B(2,3F)OCH₂B-3 | (Compound No. 163) | 2.0% |
| 5-HB-F | | 12.0% |
| 6-HB-F | | 9.0% |
| 7-HB-F | | 7.0% |
| 2-HHB-OCF₃ | | 7.0% |
| 3-HHB-OCF₃ | | 7.0% |
| 4-HHB-OCF₃ | | 7.0% |
| 5-HHB-OCF₃ | | 5.0% |
| 3-HH2B-OCF₃ | | 4.0% |
| 5-HH2B-OCF₃ | | 4.0% |
| 3-HHB(3,5F)-OCF₃ | | 5.0% |
| 3-HBB(3F)-F | | 10.0% |
| 3-HH2B(3F)-F | | 3.0% |
| 3-HB(3F)BH-3 | | 3.0% |
| 5-HBBH-3 | | 3.0% |
| 3-HHB(3,5F)-OCF₂H | | 4.0% |
| Composition Example 21 | | |
| 2O-B(2,3F)B(3F)2B-3 | (Compound No. 1) | 10.0% |
| 2-BB(2F)2B(2,3F)-3 | (Compound No. 50) | 2.0% |
| 5-H4HB(3,5F)-F | | 7.0% |
| 5-H4HB-OCF₃ | | 15.0% |
| 3-H4HB(3,5F)-CF₃ | | 8.0% |
| 5-H4HB(3,5F)-CF₃ | | 10.0% |
| 3-HB-CL | | 6.0% |
| 5-HB-CL | | 2.0% |
| 2-H2BB(3F)-F | | 5.0% |
| 5-HVHB(3,5F)-F | | 5.0% |
| 3-HHB-OCF₃ | | 5.0% |
| 3-H2HB-OCF₃ | | 5.0% |
| V-HHB(3F)-F | | 5.0% |
| 3-HHB(3F)-F | | 5.0% |
| 5-HHEB-OCF₃ | | 2.0% |
| 3-HBEB(3,5F)-F | | 5.0% |
| 5-HH-V2F | | 3.0% |
| Composition Example 22 | | |
| 2O-B(2,3F)B(3F)2B-3 | (Compound No. 1) | 15.0% |
| 2-BB(2F)2B(2,3F)-3 | (Compound No. 50) | 3.0% |
| 2-BB(2,3F)2B(2,3F)-3 | (Compound No. 62) | 3.0% |
| 2O-B(2F)B(2,3F)OCH₂B-3 | (Compound No. 163) | 3.0% |
| 2-HHB(3F)-F | | 2.0% |

| | |
|---|---|
| -continued | |
| 3-HHB(3F)-F | 2.0% |
| 5-HHB(3F)-F | 2.0% |
| 2-HBB(3F)-F | 6.0% |
| 3-HBB(3F)-F | 6.0% |
| 5-HBB(3F)-F | 10.0% |
| 2-H2BB(3F)-F | 9.0% |
| 3-H2BB(3F)-F | 9.0% |
| 3-HBB(3,5F)-F | 15.0% |
| 5-HBB(3,5F)-F | 5.0% |
| 1O1-HBBH-4 | 5.0% |
| 1O1-HBBH-5 | 5.0% |

BEST MODE FOR CARRYING OUT THE INVENTION

Now, the present invention will be described in more detail with reference to Examples. In the Examples, C indicates crystal, $S_A$: smectic phase A, $S_B$: smectic phase B, $S_X$: smectic phase the structure of which has not been defined, N: nematic phase, and Iso: isotropic phase, and the unit of all phase transition temperatures is ° C.

EXAMPLE 1

Preparation of 4-ethoxy-2,3,3'-trifluoro-4'-(2-(4-propylphenyl)ethyl)biphenyl (2O-B(2,3F)B(3F)2B-3: Compound No. 1)

(First step) Preparation of 4-ethoxy-2,3,3'-trifluorobiphenyl

Mixture of 20.0 g (79.3 mmol) of 4-ethoxy-2,3-difluoroiodobenzene [obtained by lithiating 4-ethoxy-2,3-difluorobenzene with sec-butyl lithium and then reacting with iodine], 18.9 g (118.9 mmol) of dihydroxy(3-fluorophenyl)borane [obtained by reacting a Grignard reagent, which was prepared from 3-fluorobromobenzene and magnesium, with trimethoxyborane and then hydrolyzing with hydrochloric acid], 21.9 g (158.6 mmol) of $K_2CO_3$, 2.0 g of 5% Pd—C, and 100 ml of mixed solvent of toluene/ethanol/ water (1/1/1) was heated to reflux for 13 hours. Subsequently, after the catalyst was filtered off, the mixture was subjected to extraction with toluene, and the organic layer thus obtained was washed with water thrice and then dried over anhydrous magnesium sulfate. The solvent was distilled off under a reduced pressure and the residue thus obtained was subjected to silica gel column chromatography (eluent: heptane/toluene=8/2) to obtain 17.3 g of a crude 4-ethoxy-2,3,3'-trifluorobiphenyl. (Yield: 86.2%)

This product was used without further purification for next reaction.

(Second step) Preparation of 4-ethoxy-2,3,3'-trifluoro-4'-(1-hydroxy-2-(4-propylphenyl)ethyl)biphenyl In a solution of 10.0 g (39.6 mmol) of the 4-ethoxy-2,3, 3'-trifluorobiphenyl obtained in the previous step in 50 ml of tetrahydrofuran (THF) was added dropwise 38 ml of sec-butyl lithium (1.04M, cyclohexane solution, corresponding to 39.6 mmol) while being maintained at a temperature lower than −60° C. After finishing of the dropping, the solution was stirred at the same temperature for 1 hour. Solution of 6.3 g (36.0 mmol) of 4-propylphenyl-acetaldehyde in 30 ml of THF was added dropwise to the reaction liquid while being maintained at a temperature lower than −60° C., and stirred at the same temperature for 1 hour.

After 200 ml of a diluted hydrochloric acid was added dropwise to the reaction liquid, it was extracted with 100 ml of ethyl acetate. After the organic layer thus obtained was washed with a diluted aqueous sodium bicarbonate solution twice and water thrice, it was dried over anhydrous magnesium sulfate. The solvent was distilled off under a reduced pressure and the residue thus obtained was subjected to silica gel column chromatography (eluent: heptane/ethyl acetate=8/2) to obtain 6.1 g of a crude 4-ethoxy-2,3-3'-trifluoro-4'-(1-hydroxy-2-(4-propylphenyl)ethyl)biphenyl. (Yield: 41.4%)

This product was used without further purification for next reaction.

(Third step) Preparation of 4-ethoxy-2,3,3'-trifluoro-4'-(2-(4-propylphenyl)vinyl)biphenyl Mixture of 6.1 g (14.8 mmol) of the 4-ethoxy-2,3,3'-trifluoro-4'-(1-hydroxy-2-(4-propylphenyl)ethyl)biphenyl obtained in the previous step, 0.3 g of p-toluene sulfonic acid monohydrate, and 50 ml of toluene was heated to reflux while the distilled water being taken out for 2 hours. After finishing of the reaction, the product was washed with a diluted aqueous sodium bicarbonate solution twice and water thrice, and dried over anhydrous magnesium sulfate. The solvent was distilled off under a reduced pressure and the residue thus obtained was subjected to silica gel column chromatography (eluent: heptane/toluene=6/4) to obtain 2.8 g of a crude 4-ethoxy-2,3,3'-trifluoro-4'-(2-(4-propylphenyl)vinyl)biphenyl. (Yield: 49.1%).

(Fourth step) Preparation of 4-ethoxy-2,3,3'-trifluoro-4'-(2-(4-propylphenyl)ethyl)biphenyl First, 2.8 g (7.0 mmol) of the 4-ethoxy-2,3,3'-trifluoro-4'-(2-(4-propylphenyl)vinyl)biphenyl obtained in the previous step, 0.15 g of 5% Pd—C, and 50 ml of mixed solvent of toluene/ethanol (1/1) were mixed and subjected to reduction with hydrogen. Next, after absorption of hydrogen was terminated, the catalyst was filtered off. The solvent was distilled off under a reduced pressure and the residue thus obtained was subjected to silica gel column chromatography (eluent: heptane/toluene=8/2) to obtain 2.4 g of a crude 4-ethoxy-2,3,3'-trifluoro-4'-(2-(4-propylphenyl)ethyl)biphenyl. This product was recrystallized from mixed solvent of ethanol/ethyl acetate (8/2) to obtain 1.3 g of the subject compound. (Yield: 44.6%)

This compound exhibited liquid crystal phase and its phase transition temperatures were as follows:

C 73.9~74.5 N 83.5 Iso.

Further, data of each spectrum well supported its structure. Mass analysis: 398 (M$^+$).

$^1$H-NMR (CDCl$_3$, TMS internal standard)

δ (ppm)

0.94 (t, 3H)

1.39–1.76 (m, 5H)

2.57 (t, 2H)

2.93 (s, 4H)

4.16 (q, 2H)

6.78–7.25 (m, 9H)

Example of cases in which the compounds of the present invention were used as component of liquid crystal compositions are shown below. In each of Use Examples, NI indicates the phase transition temperature (° C.) of nematic phase-isotropic phase, Δε: dielectric anisotropy value, Δn: optical anisotropy value, η: viscosity (mPa·s), Vth: threshold voltage (V), and VHR: voltage holding ratio (%).

In this connection, η was determined at 20° C., Δε, Δn, Vth, and twist pitch (μm) were determined at 25° C., and VHR indicates the value obtained by determining it at 25° C., 80° C., or 100° C. in the order from left side to right side.

EXAMPLE 2

Use Example 1

Liquid crystal composition (A) comprising the following cyanophenylcyclohexane type liquid crystalline compounds in the amount shown below

| | |
|---|---|
| 4-(trans-4-propylcyclohexyl)benzonitrile | 24% |
| 4-(trans-4-pentylcyclohexyl)benzonitrile | 36% |
| 4-(trans-4-heptylcyclohexyl)benzonitrile | 25% |
| 4-(trans-4-pentylcyclohexyl)-4'-cyanobiphenyl | 15% | had physical properties as follows:

NI: 71.7, Δε: 11.0, Δn: 0.137, η: 26.7, Vth: 1.78

Physical properties of liquid crystal composition (B) comprising 85% of the liquid crystal composition (A) and 15% of the 4-ethoxy-2,3,3'-trifluoro-4'-(2-(4-propylphenyl)ethyl)biphenyl (Compound No. 1) obtained in Example 1 were as follows:

NI: 69.0, Δε: 9.1, Δn: 0.142, η: 31.0, Vth: 1.71

While the liquid crystal composition (B) was left in a freezer kept at −20° C., development of smectic phase or separation of crystals was not observed over 60 days.

EXAMPLE 3

Use Example 2

Liquid crystal composition (C) comprising the following ester type liquid crystalline compounds in the amount shown below

| | |
|---|---|
| 3-HEB-O2 | 17.2% |
| 3-HEB-O4 | 27.6% |
| 4-HEB-O2 | 20.7% |
| 5-HEB-O1 | 20.7% |
| 5-HEB-O2 | 13.8% | had physical properties as follows:

NI: 74.0, Δε: −1.43

Physical properties of liquid crystal composition (D) comprising 85% of the liquid crystal composition (C) and 15% of the 4-ethoxy-2,3,3'-trifluoro-4'-(2-(4-propylphenyl)ethyl)biphenyl (Compound No. 1) obtained in Example 1 were as follows:

NI: 75.6, Δε: −2.04

While the liquid crystal composition (D) was left in a freezer kept at −20° C., development of smectic phase and deposition of crystals were not observed over 60 days.

Following compounds can be synthesized according to the method described in Example 1. Values of physical properties shown below are ones of liquid crystal composition determined according to the method of Example 3.

Compound No. 2: 1-B(2, 3F)B(3F)2B-3

Compound No. 3: 3-B(2, 3F)B(3F)2B-2

NI: 67.0, Δε: −1.50

Compound No. 4: 5-B(2, 3F)B(3F)2B-2

Compound No. 5: 10-B(2, 3F)B(3F)2B-2

Compound No. 6: 15-B(2, 3F)B(3F)2B-5

Compound No. 7: 3O-B(2, 3F)B(3F)2B-2

Compound No. 8: 8O-B(2, 3F)B(3F)2B-3

Compound No. 9: 20O-B(2, 3F)B(3F)2B-4

Compound No. 10: 3-B(2, 3F)B(2F)2B-3

Compound No. 11: 4-B(2, 3F)B(2F)2B-2

Compound No. 12: 12-B(2, 3F)B(2F)2B-8

Compound No. 13: 1O-B(2, 3F)B(2F)2B-5
Compound No. 14: 4O-B(2, 3F)B(2F)2B-2
Compound No. 15: 5O-B(2, 3F)B(2F)2B-1O1
Compound No. 16: 2-B(2, 3F)B2B(2F)-3
Compound No. 17: 3-B(2, 3F)B2B(2F)-4
Compound No. 18: 7-B(2, 3F)B2B(2F)-2
Compound No. 19: 3-B(2, 3F)B2B(2F)-3O1
Compound No. 20: 2O-B(2, 3F)B2B(2F)-2
Compound No. 21: 5O-B(2, 3F)B2B(2F)-3
Compound No. 22: 6O-B(2, 3F)B2B(2F)-3
Compound No. 23: 2-B(2, 3F)B2B(2F)-3
Compound No. 24: 1-B(2, 3F)B2B(3F)-5
Compound No. 25: 2-B(2, 3F)B2B(3F)-3
Compound No. 26: 3-B(2, 3F)B2B(3F)-2
Compound No. 27: 4-B(2, 3F)B2B(3F)-1
Compound No. 28: 5O1-B(2, 3F)B2B(3F)-3
Compound No. 29: 2O-B(2, 3F)B2B(3F)-O3
Compound No. 30: 3O-B(2, 3F)B2B(3F)-O2
Compound No. 31: 5O-B(2, 3F)B2B(3F)-O3
Compound No. 32: 3-B(2F)B(2, 3F)2B-5
Compound No. 33: 5-B(2F)B(2, 3F)2B-2
Compound No. 34: 1O4-B(2F)B(2, 3F)2B-3
Compound No. 35: 2O-B(2F)B(2, 3F)2B-5
Compound No. 36: 5O-B(2F)B(2, 3F)2B-2
Compound No. 37: 1-B(3F)B(2, 3F)2B-4
Compound No. 38: 3-B(3F)B(2, 3F)2B-5
Compound No. 39: 4O1-B(3F)B(2, 3F)2B-3
Compound No. 40: 3O-B(3 F)B(2, 3F)2B-3
Compound No. 41: 4O-B(3F)B(2, 3F)2B-3
Compound No. 42: 2-BB(2, 3F)2B(2F)-3
Compound No. 43: 1O-BB(2, 3F)2B(2F)-2
Compound No. 44: 2O1-BB(2, 3F)2B(2F)-3
Compound No. 45: 8O2-BB(2, 3F)2B(2F)-2
Compound No. 46: 3O-BB(2, 3F)2B(2F)-2
Compound No. 47: 4-BB(2, 3F)2B(3F)-3
Compound No. 48: 8-BB(2, 3F)2B(3F)-1O
Compound No. 49: 1O5-BB(2, 3F)2B(3F)-1O3
Compound No. 50: 2-BB(2F)2B(2, 3F)-3
Compound No. 51: 3-B(2F)B(2F)2B(2F)-2
Compound No. 52: 3O-B(2F)B(2F)2B(2F)-3
Compound No. 53: 5-B(2F)B(2F)2B(3F)-1
Compound No. 54: 2O-B(2F)B(2F)2B(3F)-1O5
Compound No. 55: 4O-B(2F)B(3F)2B(2F)-2
Compound No. 56: 5-B(2F)B(3F)2B(3F)-O3
Compound No. 57: 2-B(3F)B(2F)2B(2F)-5
Compound No. 58: 1O4-B(3F)B(2F)2B (3F)-3
Compound No. 59: 15-B(3F)B(3F)2B(2F)-2
Compound No. 60: 3-B(3F)B(3F)2B(3F)- O3
Compound No. 61: 2-B(2, 3F)B(2, 3F)2B-6
Compound No. 62: 3-B(2, 3F)2B(2, 3F)B-2
  NI: 67.8, Δε: −1.75
Compound No. 63: 4-B(2, 3F)B(2, 3F)2B-2
Compound No. 64: 6-B(2, 3F)B(2, 3F)2B-5
Compound No. 65: 1O5-B(2, 3F)B(2, 3F)2B-2
Compound No. 66: 3O-B(2, 3F)B(2, 3F)2B-1
Compound No. 67: 4O-B(2, 3F)B(2, 3F)2B-2
Compound No. 68: 5O-BB(2, 3F)2B (2, 3F)-2
Compound No. 69: 3-B(2, 3F)B2B(2, 3F)-O2
Compound No. 70: 3O-B(2, 3F)B2B(2, 3F)-O1
Compound No. 71: 3-B(2, 3F)B(2F)2B(2F)-2
Compound No. 72: 5-B(2, 3F)B(2F)2B(2F)-2
Compound No. 73: 1O3-B(2, 3F)B(2F)2B(2F)-1O2
Compound No. 74: 3O-B(2, 3F)B(2F)2B(2F)-3
Compound No. 75: 4O-B(2, 3F)B(2F)2B(2F)-4
Compound No. 76: 1-B(2, 3F)B(2F)2B(3F)-1
Compound No. 77: 3-B(2, 3F)B(2F)2B(3F)-2
Compound No. 78: 4-B(2, 3F)B(2F)2B(3F)-3
Compound No. 79: 1O5-B(2, 3F)B(2F)2B(3F)-2
Compound No. 80: 2O-B(2, 3F)B(2F)2B(3F)-3
Compound No. 81: 5O-B(2, 3F)B(2F)2B(3F)-3
Compound No. 82: 8O-B(2, 3F)B(2F)2B(3F)-3
Compound No. 83: 2O-B(2, 3F)B(2F)2B(3F)-O3
Compound No. 84: 3O-B(2, 3F)B(2F)2B(3F)-O2
Compound No. 85: 2-B(2, 3F)B(3F)2B(2F)-5
Compound No. 86: 5-B(2, 3F)B(3F)2B(2F)-2
Compound No. 87: 5O5-B(2, 3F)B(3F)2B(2F)-2
Compound No. 88: 3O-B(2, 3F)B(3F)2B(2F)-2
Compound No. 89: 4O-B(2, 3F)B(3F)2B(2F)-3
Compound No. 90: 2-B(2, 3F)B(3F)2B(3F)-5
Compound No. 91: 3-B(2, 3F)B(3F)2B(3F)-3
Compound No. 92: 5-B(2, 3F)B(3F)2B(3F)-3
Compound No. 93: 4-B(2, 3F)B(3F)2B(3F)-O2
Compound No. 94: 1O-B(2, 3F)B(3F)2B(3F)-3
Compound No. 95: 2O-B(2, 3F)B(3F)2B(3F)-2
Compound No. 96: 3O-B(2, 3F)B(3F)2B(3F)-O2
Compound No. 97: 5O-B(2, 3F)B(3F)2B(3F)-O3
Compound No. 98: 3-B(2, 3F)B(2, 3F)2B(2F)-2
Compound No. 99: 3-B(2, 3F)B(2, 3F)2B(2F)-3
Compound No. 100: 4-B(2, 3F)B(2, 3F)2B(2F)-2
Compound No. 101: 2O-B(2, 3F)B(2, 3F)2B(2F)-2
Compound No. 102: 4O-B(2, 3F)B(2, 3F)2B(2F)-5
Compound No. 103: 3O-B(2, 3F)B(2, 3F)2B(2F)-O2
Compound No. 104: 15O-B(2, 3F)B(2, 3F)2B(2F)-O 13
Compound No. 105: 2-B(2, 3F)B(2, 3F)2B(3F)-3
Compound No. 106: 2-B(2, 3F)B(2, 3F)2B(3F)-4
Compound No. 107: 3-B(2, 3F)B(2, 3F)2B(3F)-2
Compound No. 108: 3-B(2, 3F)B(2, 3F)2B(3F)-5
Compound No. 109: 3-B(2, 3F)B(2, 3F)2B(3F)-O2
Compound No. 110: 4-B(2, 3F)B(2, 3F)2B(3F)-O3
Compound No. 111: 2O-B(2, 3F)B(2, 3F)2B(3F)-O2
Compound No. 112: 3O-B(2, 3F)B(2, 3F)2B(3F)-O2
Compound No. 113: 5O-B(2, 3F)B(2, 3F)2B(3F)-O3
Compound No. 114: 1-B(2, 3F)B(2, 3F)2B(2, 3F)-3
Compound No. 115: 2-B(2, 3F)B(2, 3F)2B(2, 3F)-2
Compound No. 116: 3-B(2, 3F)B(2, 3F)2B(2, 3F)-4
Compound No. 117: 4-B(2, 3F)B(2, 3F)2B(2, 3F)-3
Compound No. 118: 5-B(2, 3F)B(2, 3F)2B(2, 3F)-O2
Compound No. 119: 7-B(2, 3F)B(2, 3F)2B(2, 3F)-O3
Compound No. 120: 1O-B(2, 3F)B(2, 3F)2B(2, 3F)-O3
Compound No. 121: 2O-B(2, 3F)B(2, 3F)2B(2, 3F)-O5
Compound No. 122: 3O-B(2, 3F)B(2, 3F)2B(2, 3F)-O2
Compound No. 123: 5O-B(2, 3F)B(2, 3F)2B(2, 3F)-O2
Compound No. 124: 2-B(2, 3F)B(2F)4B-2
Compound No. 125: 2-B(2, 3F)B(3F)4B-5
Compound No. 126: 3O-B(2, 3F)B4B(3F)-O5
Compound No. 127: 2O1-B(2F)B(2, 3F)4B-5
Compound No. 128: 7-BB(2, 3F)4B(3F)-2O1
Compound No. 129: 5O-B(2, 3F)B(2, 3F)4B-3
Compound No. 130: 2O-B(2, 3F)B4B(2, 3F)-O3
Compound No. 131: 1O1-B(2F)B(2, 3F)4B(3F)-O4
Compound No. 132: 3-B(2, 3F)B(2, 3F)4B(3F)-O6
Compound No. 133: 3-B(2, 3F)B(3F)4B(2, 3F)-2
Compound No. 134: 15-B(2, 3F)2B(3F)2B-2O
Compound No. 135: 2O-B(2, 3F)2B2B(3F)-3
Compound No. 136: 4O-B(2F)2B(2, 3F)2B-5
compound No. 137: 3-B(2, 3F)2B(2, 3F)2B-3
Compound No. 138: 2O-B(2F)2B(2, 3F)2B(3F)-1O3
Compound No. 139: 3O-B(2, 3F)2B2B(2, 3)-O2
Compound No. 140: 1O3-B(2, 3F)2B(2, 3F)2B(3F)-3
Compound No. 141: 5-B(2, 3F)2B(2F)2B(2, 3F)-2

EXAMPLE 4

Preparation of 2,3,3'-trifluoro-4'-(4-ethylphenyl) methoxy-4-propylbiphenyl (2-BCH$_2$OB(2F)B(2,3F)-3: Compound No. 142)

(First step) Preparation of 2,3,3'-trifluoro-4'-hydroxy-4-propylbiphenyl

Solution of 10.0 g (32.2 mmol) of 2,3,3'-trifluoro-4'-methoxymethoxy-4-propylbiphenyl [prepared by cross coupling reaction of 2,3-difluoro-4-propyliodobenzene with dihydroxy(3-fluoro-4-methoxymethoxyphenyl)borane in the presence of a Pd catalyst], 50 ml of methanol, and 10 ml of a concentrated hydrochloric acid was heated to reflux for 3 hours. Water in an amount of 50 ml was added to the reaction liquid and subjected to extraction with 100 ml of diethyl ether. After the organic layer thus obtained was washed with a diluted aqueous sodium bicarbonate solution twice and water thrice, it was dried over anhydrous magnesium sulfate. The solvent was distilled off under a reduced pressure to obtain 8.5 g of a crude 2,3,3'-trifluoro-4'-hydroxy-4-propylbiphenyl. (Yield: 99.8%)

This product was used without further purification to next reaction.

(Second step) Preparation of 2,3,3'-trifluoro-4'-(4-ethylphenyl)methoxy-4-propylbiphenyl In a mixture of 0.7 g (60% oiliness, corresponds to 18.0 mmol) of sodium hydride with 3 ml of dimethyl formamide (DMF) was added dropwise a solution of 4.0 g (15.0 mmol) of the 2,3,3'-trifluoro-4'-hydroxy-4-propylbiphenyl obtained in the previous step in 20 ml of DMF, and stirred at the same temperature for 1 hour.

Subsequently, a solution of 5.5 g (22.5 mmol) of 4-ethyl-1-iodomethylbenzene in 20 ml of DMF was added dropwise to the reaction liquid at room temperature, stirred at the same temperature for 1 hour, and then heated to reflux for 3 hours. After finishing of the reaction, the reaction liquid was poured into 50 ml of water and subjected to extraction with 150 ml of toluene. The organic layer thus obtained was washed with a diluted aqueous sodium hydroxide solution thrice and water thrice, and then dried over anhydrous magnesium sulfate. The solvent was distilled off under a reduced pressure and the residue thus obtained was subjected to silica gel column chromatography (eluent: heptane/toluene=7/3) to obtain 2.3 g of a crude 2,3,3'-trifluoro-4'-(4-ethylphenyl)methoxy-4-propylbiphenyl. This product was recrystallized from mixed solvent of ethanol/ethyl acetate (7/3) to obtain 1.9 g of the subject compound. (Yield: 33.3%)

EXAMPLE 5

Following compounds can be synthesized according to the method of Example 4:

Compound No. 143: 5-B(2, 3F)B(3F)OCH$_2$B-3
Compound No. 144: 12-B(2, 3F)B(3F)OCH$_2$B-4
Compound No. 145: 1O1-B(2, 3F)B(3F)OCH$_2$B -5
Compound No. 146: 3O-B(2, 3F)B(3F)OCH$_2$B-4
Compound No. 147: 5O-B(2, 3F)B(3F)OCH$_2$B-2
Compound No. 148: 2-B(2, 3F)B(3F)CH$_2$OB-4
Compound No. 149: 3-B(2, 3F)B(3F)CH$_2$OB-7
Compound No. 150: 4-B(2, 3F)B(3F)CH$_2$OB-1O3
Compound No. 151: 2O-B(2, 3F)B(3F)CH$_2$OB-5
Compound No. 152: 4O-B(2, 3F)B(3F)CH$_2$OB-2
Compound No. 153: 1-B(2, 3F)B(2F)OCH$_2$B-2
Compound No. 154: 3-B(2, 3F)B(2F)OCH$_2$B-4
Compound No. 155: 5O-B(2, 3F)B(2F)OCH$_2$B-3O1
Compound No. 156: 2-B(2, 3F)B(2F)CH$_2$OB-3
Compound No. 157: 8-B(2, 3F)B(2F)CH$_2$OB-5
Compound No. 158: 3O-B(2, 3F)B(2F) CH$_2$OB-2
Compound No. 159: 3-B(2, 3F)BOCH$_2$B(2F)-3
Compound No. 160: 5-B(2, 3F)BCH$_2$OB(2F)-2
Compound No. 161: 3O-B(2, 3F)BOCH$_2$B(3F)-O1
Compound No. 162: 8-B(2, 3F)BCH$_2$OB(3F)-7
Compound No. 163: 2O-B(2F)B(2, 3F)OCH$_2$B-3
Compound No. 164: 5-BB(2, 3F)OCH$_2$B(3F)-O2
Compound No. 165: 4-B(2, 3F)B(2, 3F)OCH$_2$B-3
Compound No. 166: 5O-B(2, 3F)B(2, 3F)CH$_2$OB-2
Compound No. 167: 3O1-B(2, 3F)B(2, 3F)OCH$_2$B-2
Compound No. 168: 6-B(2, 3F)BCH$_2$OB(2, 3F)-O2
Compound No. 169: 1O1-BB(2, 3F)CH$_2$OB(2, 3F)-O3
Compound No. 170: 12O-B(2F)B(2, 3F)OCH$_2$B(3F)-O3
Compound No. 171: 3-B(2, 3F)B(2, 3F)OCH$_2$B(2F)-2
Compound No. 172: 2O-B(2, 3F)B(2, 3F)OCH$_2$B-3
Compound No. 173: 5O-B(2, 3F)B(2, 3F)CH$_2$OB(2F)-3
Compound No. 174: 1O3-B(2, 3F)B(3F)CH$_2$OB(2, 3F)-10

EXAMPLE 6

Use Example 3

Physical properties of the liquid crystal composition of Composition Example 1 were as follows:

NI: 75.6, $\Delta\epsilon$: −2.0, $\Delta$n: 0.099, $\eta$: 21.2

While this liquid crystal composition was left in a freezer kept at −20° C., development of smectic phase and deposition of crystals were not observed more than 60 days.

EXAMPLE 7

Use Example 4

Physical properties of the liquid crystal composition of Composition Example 2 were as follows:

NI: 67.8, $\Delta\epsilon$: −1.8, $\Delta$n: 0.093, $\eta$: 22.4

While this liquid crystal composition was left in a freezer kept at −20° C., development of smectic phase and deposition of crystals were not observed more than 60 days.

EXAMPLE 8

Use Example 5

Physical properties of the liquid crystal composition of Composition Example 3 were as follows:

NI: 88.9, $\Delta\epsilon$: −3.9, $\Delta$n: 0.085, VHR: 98.1, 97.2, 96.7

While this liquid crystal composition was left in a freezer kept at −20° C., development of smectic phase and deposition of crystals were not observed more than 60 days.

EXAMPLE 9

Use Example 6

Physical properties of the liquid crystal composition of Composition Example 4 were as follows:

NI: 64.1, $\Delta\epsilon$: −2.7, $\Delta$n: 0.103

While this liquid crystal composition was left in a freezer kept at −20° C., development of smectic phase and deposition of crystals were not observed more than 60 days.

EXAMPLE 10

Use Example 7

Physical properties of the liquid crystal composition of Composition Example 5 were as follows:

NI: 74.8, $\Delta\epsilon$: −3.5, $\Delta$n: 0.199

While this liquid crystal composition was left in a freezer kept at −20° C., development of smectic phase and deposition of crystals were not observed more than 60 days.

EXAMPLE 11

Use Example 8

Physical properties of the liquid crystal composition of Composition Example 6 were as follows:

NI: 78.1, $\Delta\epsilon$: −3.0, $\Delta$n: 0.146

While this liquid crystal composition was left in a freezer kept at −20° C., development of smectic phase and deposition of crystals was not observed more than 60 days.

EXAMPLE 12

Use Example 9

Physical properties of the liquid crystal composition of Composition Example 7 were as follows:

NI: 72.2, $\Delta\epsilon$: −2.9, $\Delta$n: 0.156, $\eta$: 27.4

While this liquid crystal composition was left in a freezer kept at −20° C., development of smectic phase and deposition of crystals were not observed more than 60 days.

EXAMPLE 13

Use Example 10

Physical properties of the liquid crystal composition of Composition Example 8 were as follows:

NI: 83.1, $\Delta$n: 0.212

While this liquid crystal composition was left in a freezer kept at −20° C., development of smectic phase and deposition of crystals were not observed more than 60 days.

EXAMPLE 14

Use Example 11

Physical properties of the liquid crystal composition of Composition Example 9 were as follows:

NI: 74.6, $\Delta\epsilon$: −3.9, $\Delta$n: 0.126

While this liquid crystal composition was left in a freezer kept at −20° C., development of smectic phase and deposition of crystals were not observed more than 60 days.

EXAMPLE 15

Use Example 12

Physical properties of the liquid crystal composition of Composition Example 10 were as follows:

NI: 62.3, $\Delta\epsilon$: −5.8, $\Delta$n: 0.085, $\eta$: 42.0

While this liquid crystal composition was left in a freezer kept at −20° C., development of smectic phase and deposition of crystals were not observed more than 60 days.

EXAMPLE 16

Use Example 13

Physical properties of the liquid crystal composition of Composition Example 11 were as follows:

NI: 86.7, $\Delta\epsilon$: 6.6, $\Delta$n: 0.160, Vth: 2.19

Liquid crystal composition prepared by dissolving 0.8 part by weight of optically active compound CM-33 in 100 parts by weight of the liquid crystal composition of Composition Example 11 had a twist pitch of 11.4 $\mu$m.

While this liquid crystal composition was left in a freezer kept at −20° C., development of smectic phase and deposition of crystals were not observed more than 60 days.

EXAMPLE 17

Use Example 14

Physical properties of the liquid crystal composition of Composition Example 12 were as follows:

NI: 94.0, $\Delta\epsilon$: 5.9, $\Delta$n: 0.197, $\eta$: 36.1, Vth: 2.4

While this liquid crystal composition was left in a freezer kept at −20° C., development of smectic phase and deposition of crystals were not observed more than 60 days.

EXAMPLE 18

Use Example 15

Physical properties of the liquid crystal composition of Composition Example 13 were as follows:

NI: 65.3, $\Delta\epsilon$: 23.7, $\Delta$n: 0.119, $\eta$: 38.0, Vth: 1.01

While this liquid crystal composition was left in a freezer kept at −20° C., development of smectic phase and deposition of crystals were not observed more than 60 days.

EXAMPLE 19

Use Example 16

Physical properties of the liquid crystal composition of Composition Example 14 were as follows:

NI: 90.8, $\Delta\epsilon$: 4.5, $\Delta$n: 0.115, $\eta$: 17.4, Vth: 2.40

While this liquid crystal composition was left in a freezer kept at −20° C., development of smectic phase and deposition of crystals were not observed more than 60 days.

EXAMPLE 20

Use Example 17

Physical properties of the liquid crystal composition of Composition Example 15 were as follows:

NI: 100.1, $\Delta\epsilon$: 6.5, $\Delta$n: 0.200, $\eta$: 16.9, Vth: 2.15

While this liquid crystal composition was left in a freezer kept at −20° C., development of smectic phase and deposition of crystals were not observed more than 60 days.

EXAMPLE 21

Use Example 18

Physical properties of the liquid crystal composition of Composition Example 16 were as follows:

NI: 81.3, $\Delta\epsilon$: 6.2, $\Delta$n: 0.130, $\eta$: 14.1, Vth: 2.12

While this liquid crystal composition was left in a freezer kept at −20° C., development of smectic phase and deposition of crystals were not observed more than 60 days.

EXAMPLE 22

Use Example 19

Physical properties of the liquid crystal composition of Composition Example 17 were as follows:

NI: 85.1, $\Delta\epsilon$: 2.8, $\Delta$n: 0.091, $\eta$: 19.8, Vth: 2.70

Liquid crystal composition prepared by dissolving 0.3 part by weight of optically active compound CN in 100 parts by weight of the liquid crystal composition of Composition Example 17 had a twist pitch of 78 $\mu$m.

EXAMPLE 23

Use Example 20

Physical properties of the liquid crystal composition of Composition Example 18 were as follows:

NI: 75.0, Δε: 12.0, Δn: 0.130, η: 35.5, Vth: 1.55

While this liquid crystal composition was left in a freezer kept at −20° C., development of smectic phase and deposition of crystals were not observed more than 60 days.

EXAMPLE 24

Use Example 21

Physical properties of the liquid crystal composition of Composition Example 19 were as follows:

NI: 91.1, Δε: 4.1, Δn: 0.130, η: 21.6, Vth: 2.50

While this liquid crystal composition was left in a freezer kept at −20° C., development of smectic phase and deposition of crystals were not observed more than 60 days.

EXAMPLE 25

Use Example 22

Physical properties of the liquid crystal composition of Composition Example 20 were as follows:

NI: 84.3, Δε: 3.8, Δn: 0.095, η: 16.9, Vth: 2.61, VHR: 97.8, 96.5, 96.0

While this liquid crystal composition was left in a freezer kept at −20° C., development of smectic phase and deposition of crystals were not observed more than 60 days.

EXAMPLE 26

Use Example 23

Physical properties of the liquid crystal composition of Composition Example 21 were as follows:

NI: 68.9, Δε: 7.6, Δn: 0.096, η: 26.3, Vth: 1.90

While this liquid crystal composition was left in a freezer kept at −20° C., development of smectic phase and deposition of crystals were not observed more than 60 days.

EXAMPLE 27

Use Example 24

Physical properties of the liquid crystal composition of Composition Example 22 were as follows:

NI: 94.1, Δε: 5.4, Δn: 0.138, η: 38.8, Vth: 2.29

Liquid crystal composition prepared by dissolving 0.2 part by weight of optically active compound CM-43L in 100 parts by weight of the liquid crystal composition of Composition Example 22 had a twist pitch of 81 μm.

EXAMPLE 28

Comparative Example 1

Physical properties of liquid crystal composition (E) which was obtained in the same manner as in Example 7 with the exception that 4-ethyl-4'-(2-(2,3-difluoro-4-propylphenyl)ethyl)biphenyl (2-BB2B(2,3F)-3) described in Japanese Patent Application Laid-open No. Hei 2-4725 was used in place of 4-ethyl-2',3'-difluoro-4'-(2-(2,3-difluoro-4-propylphenyl)ethyl)bipyhenyl (Compound No. 62) used in Example 7, were as follows:

NI: 68.2, Δε: −1.5, Δn: 0.094, η: 20.7

From this fact, it has been found out that the compounds of the present invention have a high dielectric anisotropy compared with known compounds.

EXAMPLE 29

Comparative Example 2

Physical properties of liquid crystal composition (F) which was obtained in the same way as in Example 14 with the exception that 5% of compound, 4-ethyl-4'-((2,3-difluoro-4-propylphenyl)oxymethyl)biphenyl (2-BBCH$_2$OB(2,3F)-3), included in the general formula described in Japanese Patent Application Laid-open No. Hei 4-54146 and 5% of compound, 4,4"-dimethyl- 2,2",3,3"- tetrafluoroterphenyl (1-B(2,3F)BB(2,3F)-1), described in DE 3,839,213 A1 were used in place of 4-ethoxy-2,3,3'-trifluoro-4'-(2-(4-propylphenyl)ethyl)biphenyl (Compound No. 1) and 3'-fluoro-4-ethyl-4'-(2-(2,3-difluoro-4-propylphenyl)ethyl)biphenyl (Compound No. 50) both used in Example 14, were as follows:

NI: 75.9, Δε: −4.0, Δn: 0.127

When this liquid crystal composition (F) was left in a freezer kept at −20° C., smectic phase developed in 3 days.

From this fact, it has been found out that the compounds of the present invention hardly exhibit smectic phase at low temperatures compared with known compounds.

Liquid crystalline compounds of the present invention have an extremely high voltage holding ratio and low threshold voltage, are remarkably small in their dependency on temperature, hardly exhibit smectic phase, and are improved in miscibility with other liquid crystal materials. Further, novel liquid crystalline compounds having desired physical properties can be provided by selecting, for example, suitable substituents according to the present invention.

INDUSTRIAL APPLICABILITY

Accordingly, novel liquid crystal compositions which have an extremely high voltage holding ratio, are remarkably small in its dependency on temperature, have a low threshold voltage, have a properly high Δn and Δε, and are excellent in stability and miscibility with other liquid crystal materials can be provided by using the liquid crystalline compounds of the present invention as component of liquid crystal compositions. Further, such excellent liquid crystal display devices as IPS mode or VA mode can be provided by using the liquid crystal composition.

What is claimed is:

1. A liquid crystalline compound expressed by the general formula (1)

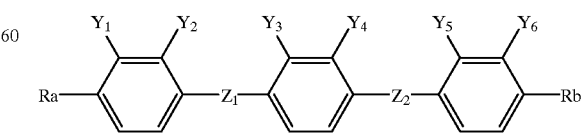

(1)

wherein Ra and Rb each independently represent a straight chain or branched alkyl group having 1 to 20 carbon atoms in which alkyl group any non-adjacent methylene group (—CH$_2$—) may be replaced by oxygen atom; Y$_1$, Y$_2$, Y$_3$, Y$_4$, Y$_5$ and Y$_6$ each independently represent hydrogen atom or fluorine atom provided that at least three of Y$_1$, Y$_2$, Y$_3$, Y$_4$, Y$_5$ and Y$_6$ represent fluorine atom; Z$_1$ and Z$_2$ independently represent —(CH$_2$)$_2$—, —(CH$_2$)$_4$—, —CH$_2$O—, —(CH$_2$)$_3$O— or single bond provided that in no case do Z$_1$ and Z$_2$ each simultaneously represent single bond; and any atom which constitutes the compound may be replaced by its isotope.

2. The liquid crystalline compound according to claim 1 wherein at least one of Z$_1$ and Z$_2$ is —(CH$_2$)$_2$— or —CH$_2$O—.

3. A liquid crystal composition comprising at least one liquid crystalline compound defined in claim 1 or 2.

4. A liquid crystal composition comprising, as a first component, at least one liquid crystalline compound defined in claim 1 or 2, and comprising, as a second component, at least one compound selected from the group consisting of the compounds expressed by any one of the general formulas (2), (3) and (4)

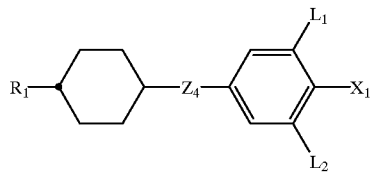

(2)

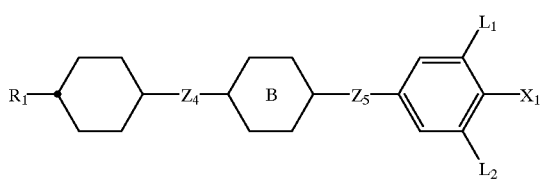

(3)

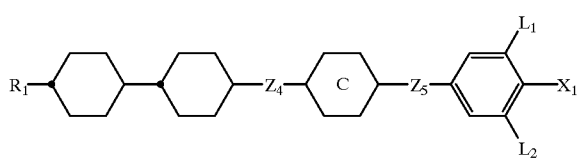

(4)

wherein R$_1$ represents an alkyl group having 1 to 10 carbon atoms in which alkyl group any non-adjacent methylene group may be replaced by oxygen atom or —CH═CH—, and any hydrogen atom in which alkyl group may be replaced by fluorine atom; X$_1$ represents fluorine atom, chlorine atom, —OCF$_3$, —OCF$_2$H, —CF$_3$, —CF$_2$H, —CFH$_2$, —OCF$_2$CF$_2$H or —OCF$_2$CFHCF$_3$; L$_1$ and L$_2$ each independently represent hydrogen atom or fluorine atom; Z$_4$ and Z$_5$ each independently represent —(CH$_2$)2—, —(CH$_2$)$_4$—, —COO—, —CF$_2$O—, —OCF$_2$—, —CH═CH— or single bond; ring B represents 1,4-phenylene in which hydrogen atom may be replaced by fluorine atom, trans-1, 4-cyclohexylene or 1,3-dioxane-2,5-diyl; ring C represents trans-1,4-cyclohexylene or 1,4-phenylene in which phenylene hydrogen atom may be replaced by fluorine atom; and any atom which constitutes these compounds may be replaced by its isotope.

5. A liquid crystal composition comprising, as a first component, at least one liquid crystalline compound defined in claim 1 or 2, and comprising, as a second component, at least one compound selected from the group consisting of the compounds expressed by the general formula (5) or (6)

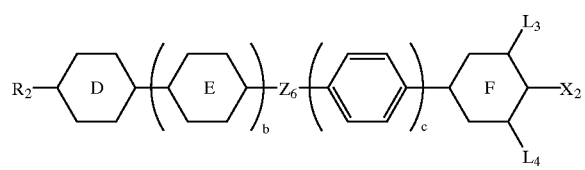

(5)

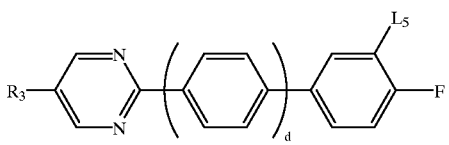

(6)

wherein R$_2$ and R$_3$ each independently represent an alkyl group having 1 to 10 carbon atoms in which alkyl group any non-adjacent methylene group may be replaced by oxygen atom or —CH═CH, and any hydrogen atom in which alkyl group may be replaced by fluorine atom; X$_2$ represents —CN group or —C≡C—CN; ring D represents trans-1,4-cyclohexylene, 1,4-phenylene, 1,3-dioxane-2,5-diyl or pyrimidine-2,5-diyl; ring E represents 1,4-phenylene in which hydrogen atom may be replaced by fluorine atom, trans-1,4-cyclohexylene or pyrimidine-2,5-diyl; ring F represents trans-1,4-cyclohexylene or 1,4-phenylene; Z$_6$ represents —(CH$_2$)$_2$—, —COO—, or single bond; L$_3$, L$_4$, and L$_5$ each independently represent hydrogen atom or fluorine atom; b, c and d are each independently 0 or 1; and any atom which constitutes these compounds may be replaced by its isotope.

6. A liquid crystal composition comprising, as a first component, at least one liquid crystalline compound defined in claim 1 or 2, and comprising, as a second component, at least one compound selected from the group consisting of the compounds expressed by any one of the general formulas (10), (11) and (12)

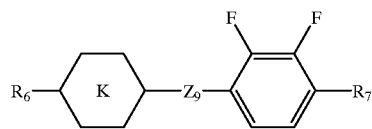

(10)

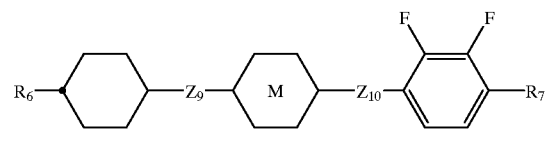

(11)

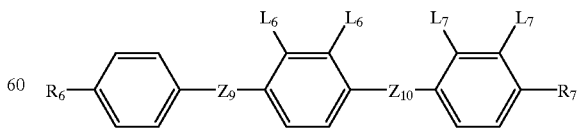

(12)

wherein R$_6$ and R$_7$ each independently represent an alkyl group having 1 to 10 carbon atoms in which alkyl group any non-adjacent methylene group may be replaced by oxygen atom or —CH═CH—, and any hydrogen atom in the alkyl group may be replaced by fluorine atom; ring K and ring M each independently represent trans-1,4-cyclohexylene or 1,4-phenylene; $L_6$ and $L_7$ each independently represent hydrogen atom or fluorine atom provided that in no case represent $L_6$ and $L_7$ simultaneously hydrogen atom; $Z_9$ and $Z_{10}$ each independently represent —(CH$_2$)$_2$—, —COO— or single bond; and any atom which constitutes these compounds may be replaced by its isotope.

7. A liquid crystal composition further comprising one or more optically active compounds in addition to the liquid crystal composition defined in claim 3.

8. A liquid crystal display device fabricated by using the liquid crystal composition defined in claim 7.

9. A liquid crystal composition comprising, as a first component, at least one liquid crystalline compound defined in claim 1 or 2, comprising, as a second component, at least one compound selected from the group consisting of the compounds expressed by any one of the general formulas (2), (3) and (4), and comprising, as a third component, at least one compound selected from the group consisting of the compounds expressed by any one of the general formulas (7), (8), and (9)

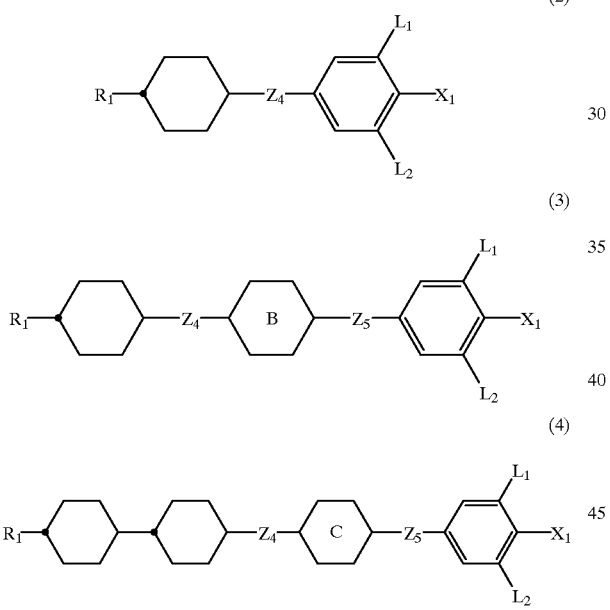

(2)

(3)

(4)

wherein $R_1$ represents an alkyl group having 1 to 10 carbon atoms in which alkyl group any non-adjacent methylene group may be replaced by oxygen atom or —CH=CH—, and any hydrogen atom in which alkyl group may be replaced by fluorine atom; $X_1$ represents fluorine atom, chlorine atom, —OCF$_3$, —OCF$_2$H, —CF$_3$, —CF$_2$H, —CFH$_2$, —OCF$_2$CF$_2$H or —OCF$_2$CFHCF$_3$; $L_1$ and $L_2$ each independently represent hydrogen atom or fluorine atom; $Z_4$ and $Z_5$ each independently represent —(CH$_2$)$_2$—, —(CH$_2$)$_4$—, —COO—, —CF$_2$O—, —OCF$_2$—, —CH=CH— or single bond; ring B represents 1,4-phenylene in which hydrogen atom may be replaced by fluorine atom, trans-1,4-cyclohexylene or 1,3-dioxane-2,5-diyl; ring C represents trans-1,4-cyclohexylene or 1,4-phenylene in which phenylene hydrogen atom may be replaced by fluorine atom; and any atom which constitutes these compounds may be replaced by its isotope,

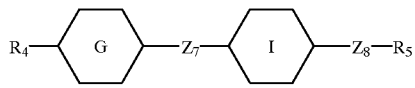

(7)

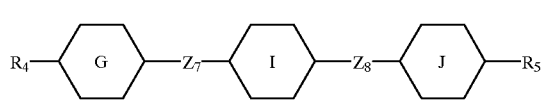

(8)

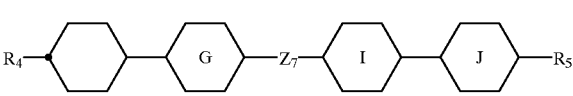

(9)

wherein $R_4$ and $R_5$ each independently represent an alkyl group having 1 to 10 carbon atoms in which alkyl group any non-adjacent methylene group may be replaced by oxygen atom or —CH=CH—, and any hydrogen atom in which alkyl group may be replaced by fluorine atom; ring G, ring I and ring J each independently represent 1,4-phenylene in which hydrogen atom may be replaced by fluorine atom, trans-1,4-cyclohexylene or pyrimidine-2,5-diyl; $Z_7$ and $Z_8$ independently represent —C≡C—, —COO—, —(CH$_2$)$_2$—, —CH=CH— or single bond; and any atom which constitutes these compounds may be replaced by its isotope.

10. A liquid crystal composition comprising, as a first component, at least one liquid crystalline compound defined in claim 1 or 2, comprising, as a second component, at least one compound selected from the group consisting of the compounds expressed by the general formula (5) or (6), and comprising, as a third component, at least one compound selected from the group consisting of the compounds expressed by any one of the general formulas (7), (8) and (9)

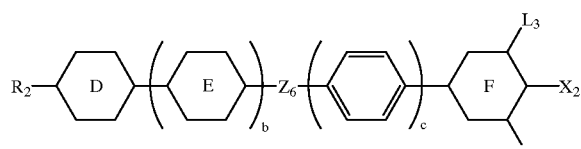

(5)

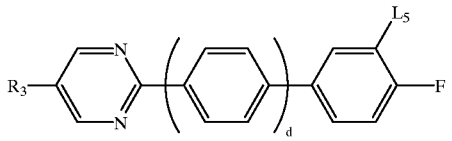

(6)

wherein $R_2$ and $R_3$ each independently represent an alkyl group having 1 to 10 carbon atoms in which alkyl group any non-adjacent methylene group may be replaced by oxygen atom or —CH=CH, and any hydrogen atom in which alkyl group may be replaced by fluorine atom; $X_2$ represents —CN group or —C≡C—CN; ring D represents trans-1,4-cyclohexylene, 1,4-phenylene, 1,3-dioxane-2,5-diyl or pyrimidine-2,5-diyl; ring E represents 1,4-phenylene in which hydrogen atom may be replaced by fluorine atom, trans-1,4-cyclohexylene or pyrimidine-2,5-diyl; ring F represents trans-1,4-cyclohexylene or 1,4-phenylene; $Z_6$ represents —(CH$_2$)$_2$—, —COO—, or single bond; $L_3$, $L_4$, and $L_5$ each independently represent hydrogen atom or fluorine atom; b, c and d are each independently 0 or 1; and any atom which constitutes these compounds may be replaced by its isotope,

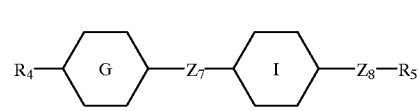 (7)

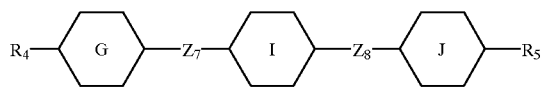 (8)

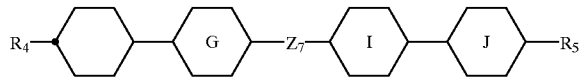 (9)

wherein $R_4$ and $R_5$ each independently represent an alkyl group having 1 to 10 carbon atoms in which alkyl group any non-adjacent methylene group may be replaced by oxygen atom or —CH=CH—, and any hydrogen atom in which alkyl group may be replaced by fluorine atom; ring G, ring I and ring J each independently represent 1,4-phenylene in which hydrogen atom may be replaced by fluorine atom, trans-1,4-cyclohexylene or pyrimidine-2,5-diyl; $Z_7$ and $Z_8$ independently represent —C≡C—, —COO—, —(CH$_2$)$_2$—, —CH=CH— or single bond; and any atom which constitutes these compounds may be replaced by its isotope.

11. A liquid crystal composition comprising, as a first component, at least one liquid crystalline compound defined in claim 1 or 2, comprising, as a second component, at least one compound selected from the group consisting of the compounds expressed by any one of the general formulas (7), (8) and (9), and comprising, as a third component, at least one compound selected from the group consisting of the compounds expressed by any one of the general formulas (10), (11) and (12)

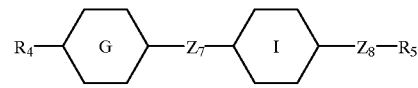 (7)

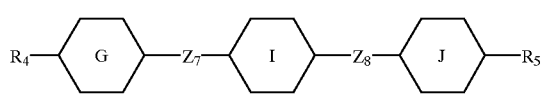 (8)

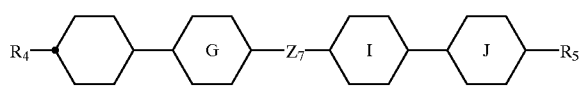 (9)

wherein $R_4$ and $R_5$ each independently represent an alkyl group having 1 to 10 carbon atoms in which alkyl group any non-adjacent methylene group may be replaced by oxygen atom or —CH=CH—, and any hydrogen atom in which alkyl group may be replaced by fluorine atom; ring G, ring I and ring J each independently represent 1,4-phenylene in which hydrogen atom may be replaced by fluorine atom, trans-1,4-cyclohexylene or pyrimidine-2,5-diyl; $Z_7$ and $Z_8$ independently represent —C≡C—, —COO—, —(CH$_2$)$_2$—, —CH=CH— or single bond; and any atom which constitutes these compounds may be replaced by its isotope,

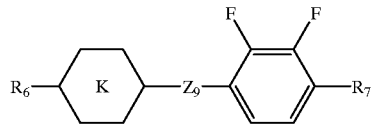 (10)

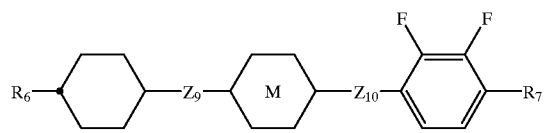 (11)

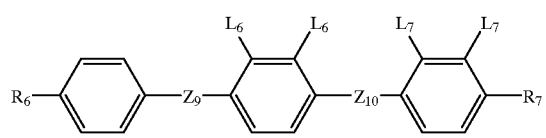 (12)

wherein $R_6$ and $R_7$ each independently represent an alkyl group having 1 to 10 carbon atoms in which alkyl group any non-adjacent methylene group may be replaced by oxygen atom or —CH=CH—, and any hydrogen atom in the alkyl group may be replaced by fluorine atom; ring K and ring M each independently represent trans-1,4-cyclohexylene or 1,4-phenylene; $L_6$ and $L_7$ each independently represent hydrogen atom or fluorine atom provided that in no case represent $L_6$ and $L_7$ simultaneously hydrogen atom; $Z_9$ and $Z_{10}$ each independently represent —(CH$_2$)$_2$—, —COO— or single bond; and any atom which constitutes these compounds may be replaced by its isotope.

12. A liquid crystal composition comprising, as a first component, at least one liquid crystalline compound defined in claim 1 or 2, comprising, as a second component, at least one compound selected from the group consisting of the compounds expressed by any one of the general formulas (2), (3) and (4), comprising, as a third component, at least one compound selected from the group consisting of the compounds expressed by the general formula (5) or (6), and comprising, as a fourth component, at least one compound selected from the group consisting of the compounds expressed by any one of the general formulas (7), (8) and (9)

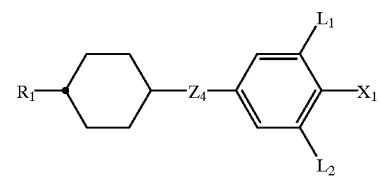 (2)

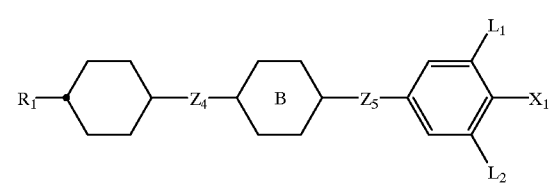 (3)

(4)

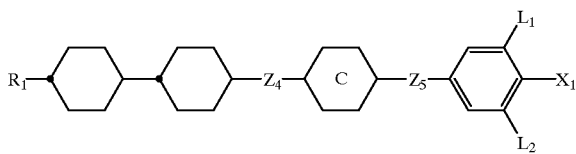

wherein $R_1$ represents an alkyl group having 1 to 10 carbon atoms in which alkyl group any non-adjacent methylene group may be replaced by oxygen atom or —CH═CH—, and any hydrogen atom in which alkyl group may be replaced by fluorine atom; $X_1$ represents fluorine atom, chlorine atom, —OCF$_3$, —OCF$_2$H, —CF$_3$, —CF$_2$H, —CFH$_2$, —OCF$_2$CF$_2$H or —OCF$_2$CFHCF$_3$; $L_1$ and $L_2$ each independently represent hydrogen atom or fluorine atom; $Z_4$ and $Z_5$ each independently represent —(CH$_2$)$_2$—, —(CH$_2$)$_4$—, —COO—, —CF$_2$O—, —OCF$_2$—, —CH═CH— or single bond; ring B represents 1,4-phenylene in which hydrogen atom may be replaced by fluorine atom, trans-1,4-cyclohexylene or 1,3-dioxane-2,5-diyl; ring C represents trans-1,4-cyclohexylene or 1,4-phenylene in which phenylene hydrogen atom may be replaced by fluorine atom; and any atom which constitutes these compounds may be replaced by its isotope, (5)

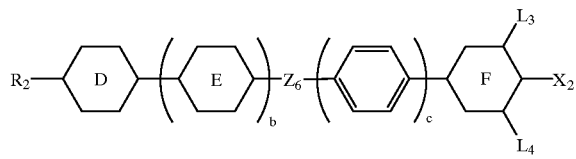

(6)

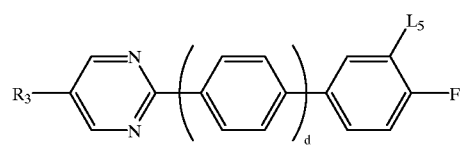

wherein $R_2$ and $R_3$ each independently represent an alkyl group having 1 to 10 carbon atoms in which alkyl group any non-adjacent methylene group may be replaced by oxygen atom or —CH═CH, and any hydrogen atom in which alkyl group may be replaced by fluorine atom; $X_2$ represents —CN group or —C≡C—CN; ring D represents trans-1,4-cyclohexylene, 1,4-phenylene, 1,3-dioxane-2,5-diyl or pyrimidine-2,5-diyl; ring E represents 1,4-phenylene in which hydrogen atom may be replaced by fluorine atom, trans-1,4-cyclohexylene or pyrimidine-2,5-diyl; ring F represents trans-1,4-cyclohexylene or 1,4-phenylene; Z6 represents —(CH$_2$)$_2$—, —COO—, or single bond; $L_3$, $L_4$, and $L_5$ each independently represent hydrogen atom or fluorine atom; b, c and d are each independently 0 or 1; and any atom which constitutes these compounds may be replaced by its isotope, (7)

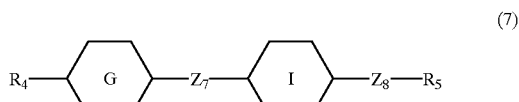

(8)

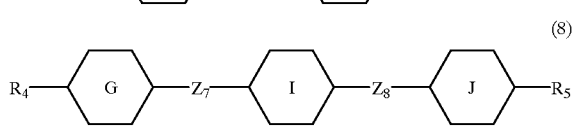

(9)

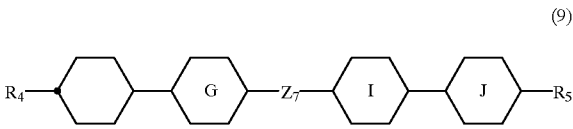

wherein $R_4$ and $R_5$ each independently represent an alkyl group having 1 to 10 carbon atoms in which alkyl group any non-adjacent methylene group may be replaced by oxygen atom or —CH═CH—, and any hydrogen atom in which alkyl group may be replaced by fluorine atom; ring G, ring I and ring J each independently represent 1,4-phenylene in which hydrogen atom may be replaced by fluorine atom, trans-1,4-cyclohexylene or pyrimidine-2,5-diyl; $Z_7$ and $Z_8$ independently represent —C≡C—, —COO—, —(CH$_2$)$_2$—, —CH═CH— or single bond; and any atom which constitutes these compounds may be replaced by its isotope.

* * * * *